United States Patent
Aldous et al.

[11] Patent Number: 5,846,986
[45] Date of Patent: Dec. 8, 1998

[54] THERAPEUTIC PHENOXYALKYLAZOLES AND PHENOXYALKYLAZINES

[75] Inventors: David J. Aldous, Glenmore; Thomas R. Bailey, Phoenixville; Guy Dominic Diana; Theodore J. Nitz, both of Pottstown, all of Pa.; Gee-Hong Kuo, Belle Mead, N.J.

[73] Assignee: Sanofi, France

[21] Appl. No.: 978,233

[22] Filed: Nov. 25, 1997

Related U.S. Application Data

[62] Division of Ser. No. 693,530, Aug. 2, 1996, Pat. No. 5,721,261, which is a division of Ser. No. 242,752, May 13, 1994, Pat. No. 5,552,420.

[51] Int. Cl.$^6$ .......................... L07D 413/12; N01K 31/41
[52] U.S. Cl. .......................... 514/364; 514/242; 514/374; 514/381; 544/182; 544/405; 548/131; 548/235; 548/252
[58] Field of Search ...................... 548/131, 235, 548/252; 544/182, 405; 514/242, 374, 381, 364

[56] References Cited

U.S. PATENT DOCUMENTS 5,648,368 7/1997 Egbertson .............................. 514/331

FOREIGN PATENT DOCUMENTS

WO/ 9412181 6/1994 WIPO.

OTHER PUBLICATIONS

Harper, J. Med. Chem. 35, 1191 (1992).

*Primary Examiner*—Robert Gerstl
*Attorney, Agent, or Firm*—Michael D. Alexander; Mary P. Bauman; Paul Dupont

[57] ABSTRACT

Compounds of the formula

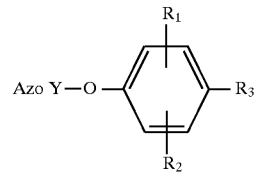

Formula I wherein

Azo is alkyltetrazolyl or is chosen from the group consisting of oxadiazolyl, imidazolyl, pyrazolyl, triazolyl, oxazolyl, triazinyl, thiazolyl, isothiazolyl or any of these substituted with a member of the group consisting of alkyl, alkylthio, alkoxy, hydroxy, halo, cyano, nitro, hydroxyalkyl, alkoxyalkyl, alkoxycarbonyl, alkanoyl, fluoroalkyl or the N-oxide of any of the preceding;

Y is an alkylene bridge of 3–9 carbon atoms;

$R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkoxycarbonyl, alkyltetrazolyl, phenyl or a heterocycle chosen from benzoxazolyl, benzathiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, tetrazolyl, thiophenyl, pyridyl, pyrimidinyl, pyrazinyl, pyridazinyl or substituted phenylor substituted heterocyclyl wherein the substitution is with alkyl, alkoxyalkyl, cycloalkyl, haloalkyl, hydroxyalkyl, alkoxy, hydroxy, furyl, thienyl or fluoroalkyl; the N-oxide thereof; or a pharmaceutically acceptable acid addition salt thereof is an effective antipicornaviral agents.

13 Claims, No Drawings

THERAPEUTIC PHENOXYALKYLAZOLES AND PHENOXYALKYLAZINES

CROSS REFERENCE TO RELATED APPLICATIONS

This application is a division of our prior application Ser. No. 08/693,530, filed Aug. 2, 1996, now U.S. Pat. No. 5,721,261, which in turn is a division of our prior application Ser. No. 08/242,752, filed May 13, 1994, now U.S. Pat. No. 5,552,420, issued Sep. 3, 1996.

BACKGROUND OF THE INVENTION

FIELD OF THE INVENTION

This invention relates to novel heterocyclic substituted phenoxyalkylazines and phenoxyalkylazoles, to methods of preparation thereof and to methods of use thereof as antipicornaviral agents.

SUMMARY OF THE INVENTION

It has now been found that compounds of Formula I are effective antipicornaviral agents. Accordingly, the present invention relates to a compound of the formula

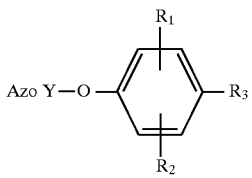

Formula I wherein

Azo is alkyltetrazolyl or is chosen from the group consisting of triazinyl, oxadiazolyl, imidazolyl, triazolyl, pyrazolyl, oxazolyl, thiazolyl, isothiazolyl or any of these substituted with a member of the group consisting of alkyl, alkylthio, alkoxy, hydroxy, halo, cyano, nitro, hydroxyalkyl, alkoxycarbonyl, alkoxyalkyl, alkanoyl, and fluoroalkyl; or the N-oxide of any of the preceding;

Y is an alkylene bridge of 3–9 carbon atoms;

$R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkoxycarbonyl, alkyltetrazolyl, phenyl or a heterocycle chosen from benzoxazolyl, benzothiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, thiophenyl, pyridyl, pyrimidinyl, pyrazinyl, pyridazinyl or substituted phenyl or substituted heterocyclyl wherein the substitution is with alkyl, alkoxyalkyl, cycloalkyl, haloalkyl, hydroxyalkyl, alkoxy, hydroxy, furyl, thienyl or fluoroalkyl is an N-oxide thereof, or a pharmaceutically acceptable acid addition salt thereof.

The invention also relates to compositions for combating picornaviruses comprising an antipicornavirally effective amount of a compound of Formula I with a suitable carrier or diluent, and to methods of combating picornaviruses therewith, including the systemic treatment of picornaviral infections in a mammalian host.

DETAILED DESCRIPTION OF PREFERRED EMBODIMENTS

Compounds of Formula I are useful as antipicornaviral agents, and are further described hereinbelow.

Alkyl and alkoxy mean aliphatic radicals, including branched radicals, of from one to five carbon atoms. Thus the alkyl moiety of such radicals include, for example methyl, ethyl, propyl, isopropyl, n-butyl, sec-butyl, t-butyl and pentyl and the like.

Cycloalkyl means an alicyclic radical having from three to seven carbon atoms as illustrated by cyclopropyl, cyclobutyl, cyclopentyl, cycloheptyl, and cyclohexyl; and Halo means bromo, chloro, iodo or fluoro.

Heterocyclyl or Het refers to a 5 or 6 membered carbon based heterocycle radical, having from one to about four nitrogen atoms and/or one oxygen or sulfur atom, provided that no two oxygen and/or sulfur atoms are adjacent in the heterocycle. Examples of these include furyl, oxazolyl, isoxazolyl, pyrazyl, imidazolyl, thiazolyl, tetrazolyl, thienyl, pyridyl, oxadiazolyl, thiadiazolyl, triazinyl, pyrimidinyl and the like.

The term heterocyclyl includes all known isomeric radicals of the described heterocycles unless otherwise specified, for example, thiadiazolyl encompasses 1,3,4-thiadiazol-2-yl, 1,2,4-thiadiazol-5-yl, and 1,2,4-thiadiazol-3-yl; thiazolyl encompasses 2-thiazolyl, 4-thiazolylyl and 5-thiazolyl and the other known variations of known heterocyclyl radicals. Thus any isomer of a named heterocycle radical is contemplated. These heterocycle radicals can be attached via any available nitrogen or carbon, for example, tetrazolyl contemplates 5-tetrazolyl or tetrazolyl attached via any available nitrogen of the tetrazolyl ring; furyl encompasses furyl attached via any available carbon, etc. The preparation of such isomers are well known and well within the scope of skilled artisan in medicinal or organic chemistry.

Certain heterocycles can exist as tautomers, and the compounds as described, while not explicity describing each tautomeric form, are meant to embrace each and every tautomer. For example, pyridinone and hydroxy pyridine radicals are tautomers. Thus the compounds of formula I depicted as having hydroxy pyridine radicals as $R_3$ of the compounds are understood to include the tautomeric pyridinones. Any tautomeric form of any heterocycle is thus also included within the scope of the description.

In the use of the terms hydroxyalkyl and alkoxyalkyl, it is understood that the hydroxy and alkoxy groups can occur at any available position of the alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2-, 3-, 4- and 5-hydroxypentyl and the like; alkoxy refers to the corresponding alkyl ethers thereof.

In the use of the term hydroxyalkoxy, it is understood that the hydroxy group can occur at any available position of alkoxy other than the C-1 (geminal) position. Thus hydroxyalkoxy includes, for example, 2-hydroxyethoxy, 2-hydroxypropoxy, 2-hydroxyisopropoxy, 5-hydroxypentoxy and the like.

Alkylene refers to a linear or branched divalent hydrocarbon radical of from 1 to about 5 carbon atoms such as methylene, 1,2-ethylene, 1,3-propylene, 1,4-butylene, 1,5-pentylene, 1,4-(2-methyl)butylene and the like. Alkylene can also have alkenyl or alkynyl linkages therein.

Halogen refers to the common halogens fluorine, chlorine, bromine and iodine.

As used herein, the term haloalkyl refers to a halo substituted alkyl, such as fluoroalkyl, chlorofluoroalkyl, bromochloroalkyl, bromofluoroalkyl, bromoalkyl, iodoalkyl, chloroalkyl and the like where the haloalkyl has one or more than one of the same or different halogens substituted for a hydrogen. Examples of haloalkyl include chlorodifluoromethyl, 1-chloroethyl, 2,2,2 trichloroethyl, 1,1 dichloroethyl, 2-chloro, 1,1,1,2 tetrafluoroethyl, bromoethyl and the like.

As used herein the term fluoroalkyl is a prefered subclass of haloalkyl, and refers to fluorinated and perfluorinated alkyl, for example fluoromethyl, difluoromethyl, trifluoromethyl, 2,2,2-trifluoroethyl, 1,2-difluoroethyl, 1,1,2,3-tetrafluorobutyl and the like.

The compounds of Formula I wherein $R_3$ is a basic nitrogen containing heterocycle are sufficiently basic to form acid addition salts and are useful both in the free base form and the form of acid-addition salts, and both forms are within the purview of the invention. The acid-addition salts are, in some cases, a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds can be prepared by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or by concentration of the solution or by any one of several other known methods. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

Alternatively, the N-oxide of those compounds having nitrogen heterocycles can be prepared by exposing the compound of the invention to a peroxide such as m-chloroperbenzoic acid and the like. These N-oxides have similar activity to their free base analogs.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC) or other art recognized means of monitoring organic reactions.

As described herein a noninteracting solvent can be N-methyl pyrrolidine (NMP), methylene chloride ($CH_2Cl_2$), tetrahydrofuran (THF), benzene or any other solvent that will not take part in the reaction. In a preferred method, the preparation of compounds of the invention is done in dried solvents under an inert atmosphere. Certain reagents used in example preparations are specified by abbreviation: triphenylphosphine (TPP), lithium aluminum hydride (LAH), triethylamine (TEA), diisopropylethylamine (DIPEA), and diethyl azodicarboxylate (DEAD). Ether is diethyl ether unless otherwise specified.

Compounds of Formula I can be prepared by several methods:

Compounds of Formula I can be prepared by the reaction of the appropriate hydroxy-Y-(Azo) and the appropriate 4-substituted phenol by the reaction described in U.S. Pat. No. 5,242,924, incorporated herein by reference.

Compounds of Formula I can be prepared by reaction of the appropriate phenol and the appropriate halo-Y-(Azo) as described in U.S. Pat. No. 4,942,241, incorporated herein by reference.

Compounds of formula I can be prepared by reaction of the appropriate phenol with a suitably X-Y-halide or X-Y-OH compound wherein X is a functional group which can be elaborated into or substituted by a heterocycle of (Azo) type by the methods described above. The azole or azine moiety is then elaborated in a final step in the synthesis. This method is preferred were the azole or azine (Azo) is triazine, thiazolyl, oxadiazolyl and the like.

Alternatively, a suitably functionalized azole or azine moiety is substituted onto the X-Y-O[$R_1$-$R_2$-$R_3$-phenyl] compound in the final step. For example, a preferred method of preparation of molecules where Azo is imidazole comprises the formation of a halo-Y-O-R1-R2-R3-phenyl compound and reacting it with imidazole to form a 1-imidazolyl compound of formula I. Alternatively a functionalized imidazole, such as a tin-imidazole derivative can be reacted with Y-O-$R_1$-$R_2$-$R_3$-phenyl compound wherein Y contains terminal unsaturation, yielding, for example, the 5 imidazolyl compound of formula I. These coupling methods are preferred when Azo is imidazolyl, pyrazolyl and the like.

Where $R_3$ is phenyl or heterocyclyl, compounds of formula I can also be prepared by reacting the hydroxy-Y-(Azo) or halo-Y-(Azo) moiety with an appropriate 4-functionalized-$R_1$-$R_2$-phenol, using the methods described above. The resulting Azo-Y-[4-functionalized $R_1$-$R_2$-phenyl] compound is then reacted with a functionalized heterocycle or phenyl ring to provide a compound where $R_3$ is phenyl or heterocyclyl. For example, a 4-borate substituted phenoxy compound is reacted with a halopyridine, for example 4-bromopyridine, to give a compound of formula I wherein $R_3$ is 4-pyridyl. Alternatively, the 4-functionalized group on the phenoxy ring can be chosen so that it can be elaborated into a heterocycle in the final steps of the synthesis. This method is preferred with $R_3$ heterocycles having 2 or more heteroatoms, such as 5-halo alkyl-1,2,4 oxadiazolyl and the like.

For example, the compound of Formula I can be prepared from an appropriate 4-substituted $R_1$, $R_2$ phenoxy-Y-(Azo) species, wherein the 4-phenoxy position is functionalized with the desired heterocycle precursor. For example, 4-[Azo)-Y-O-$R_1$-$R_2$-]benzaldehydes, and 4-[(Azo)-Y-O-$R_1$-$R_2$-]benzonitriles are prepared from known materials using methods well known in the art. [It will be understood that when ω-(Azo)-Y- is replaced by a suitable protecting group, this method will produce protected phenol, which is then deprotected to yield a phenol. This phenol is then useful in preparing the compound of formula I when reacted with the appropriate ω-(Azo)alkanol or ω-(Azo)alkylhalide.] The heterocycle on the phenoxy ring may be elaborated in a final step when preparing a compound of formula I. Suitable functionality in the 4-phenoxy position will depend upon the heterocycle sought in the final product. For example, where Het is 1,2,4-oxadiazolyl

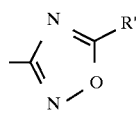

compounds are prepared from the appropriate 4-[Z-O-R$_1$-R$_2$-]benzonitrile, where z is Y-(Azo) if the target compound is a compound of formula I, by reaction with hydroxylamine hydrochloride in a noninteracting solvent, preferably pyridine or an alkanol, for example, methanol, ethanol, n-butanol, and the like, in the presence of a base, such as potassium carbonate, at a temperature between ambient temperature and the boiling point of the solvent. The product thus obtained is then reacted with an acid anhydride of formula (R'CO)$_2$O, (where R' is alkyl, haloalkyl); with R' appearing as a substituent on R$_3$ of the product. For example trifluoroacetic anyhdride, or acetic anhydride, yield trifluormethyl or methyl as R' respectively. The product is a compound of formula I where the starting material is the 4-cyano R$_1$-R$_2$-phenoxy-4-(Azo). Alternatively, if Z, is a protecting group a 4-[ZO-R$_1$-R$_2$-]phenyl(R')oxadiazole is prepared from the 4-ZO-R$_1$-R$_2$-benzonitrile, which is then deprotected and used in one of the methods described above.

Where the compound of formula I has the same heterocyle at both ends of the molecule, these heterocycles can also be elaborated at the same time from a suitable precursor by adding the appropriate excess of reactants, and using the standard reaction conditions.

It will be appreciated that neither the timing of the elaboration of the heterocyclic substituents nor the order of assembly of the intermediate is crucial to the successful synthesis of compounds of Formula I. Thus by judicious choice of reactants one can prepare any of the compounds of Formula I, by several different routes.

However, the skilled artisan will immediately recognize that the synthesis may be more successful when performing steps in a certain order so as to avoid side products. For example, the skilled artisan will appreciate that certain of the heterocycles disclosed herein are susceptible to nucleophilic attack. This susceptibility may cause undesired side products caused by elaborating the (Azo) heterocycle or the R$_3$ heterocycle before the coupling of the phenoxy an alkyl halide or alkanol moiety. The susceptibility to nucleophiles is also a consideration when determining which heterocycle is to be elaborated, for example if the phenoxyalkyl moiety has been formed, but lacks Azo and R$_3$ heterocycles. For example, a prefered method of preparing compounds of formula I wherein R$_3$ is trifluoromethyl oxadiazolyl, is to form the (Azo) -Y-O-(R$_1$-R$_2$) benzonitrile and elaborate the oxadiazolyl moiety last, to avoid any undesired side reactions. As a further example, triazines as R$_3$ or (Azo) (and other π deficient rings) are elaborated after formation of the phenoxyalkyl moiety. These considerations are spelled out in detail in Katritzky and Rees *Comprehensive Heterocyclic Chemistry* (1984).

When preparing compounds of formula I it is advantageous to arrange the order of synthesis so that yields are maximized, thus elaboration of heterocycles which are nucleophile-susceptible may be delayed until late in the synthesis. In such cases it may be advantageous to prepare a functionalized precursor in the position of the heterocycle such as ester, amide, cyano group and the like; then elaborate the heterocycle therefrom. For example a preferred method of preparing a compound wherein Azo is 2-alkyl tetrazolyl is to prepare the corresponding cyanoalkoxyphenyl heterocycle or cyano alkoxy phenyl heterocycle precursor. Other processes will be understood by analogy.

The phenols used to prepare compounds of Formula I are generally known in the art or they can be prepared by known methods. Their preparation is described in U.S. Pat. Nos. 4,942,241; 4,945,164; 5,051,437; 5,002,960; 5,110,821; 4,939,267; 4,861,971; 4,857,539; 5,242,924; or 4,843,087 incorporated herein by reference. Any phenol disclosed in these patents, or known in the art, can be reacted with a hydroxy-Y-(Azo) or halo-Y-(Azo) moiety to prepare compounds of formula I. Of course, other known phenols can be used to prepare compounds of formula I. Examples include any 4-phenylphenols, or 4-alkoxycarbonylphenols, substituted or unsubstituted as described above, all of which are well known and useful.

In addition, R$_3$-phenols (R$_3$=heterocycle) can be prepared from the suitably protected phenols which have been functionalized at the 4 position by a group such as cyanide, aldehyde, halide, acid chloride group or the like, as described above or in U.S. Pat. Nos. 4,942,241; 4,945,164; 5,051,437; 5,002,960; 5,110,821; 4,939,267; 4,861,971; 4,857,539; 5,242,924; or 4,843,087 each incorporated herein by reference, to obtain the the corresponding 4-heterocyclyl phenol by means well known in the art.

Hydroxy-Y-(Azo) or halo-Y-(Azo) compounds are prepared from known (Azo)halides, (Azo)-alcohols, (Azo)-acids or (Azo)-carboxyalkyl compounds or from any other known (Azo) species that can be suitably functionalized by known methods. For a review of reaction methods, see Katritsky and Rees, *Comprehensive Heterocyclic Chemistry* Volume 2, especially sections 2.12–2.14 (Pergamon, 1984). This reaction method is analogous to the method described for preparing compounds of formula I from X functionalized-Y-O-R$_1$-R$_2$-R$_3$-phenyl compounds.

For example, thiazole triflate, can be reacted with a terminally unsaturated tin species of formula X-Y-Z where Y has unsaturation where X=SnR$_n$, and where Z is a different functional group, not taking part in this reaction. For example, tributyltin alkynyl species, terminally unsaturated esters, acids or alcohols; such as alkynyl alkanols, α,β unsaturated esters and the like, are all useful as intermediates. The resulting unsaturated alkanols, esters and acids may be partially or completely reduced by known methods. Such reduction methods include, but are not limited to; palladium or carbon, lithium aluminum hydride and the like to give the corresponding alkanol. Alternatively, such alkanols may be prepared by reaction of (Azo) ketones, aldehydes and the like with phosphonates and the like, for example under Wittig conditions, to yield the corresponding unsaturated species which can be reduced as described above.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; alkylation of phenyl or other aromatic and heterocyclic substituents; cleavage of alkyl or benzyl ethers to produce the corresponding alcohols or phenols; and hydrolysis of esters or amides to produce the corresponding acids, alcohols or amines, preparation of anhydrides, acid halides, aldehydes, simple aromatic alkylation and the like as desired can be carried out.

Moreover, it will be appreciated that obtaining the desired product by some reactions will be better facilitated by blocking or rendering certain functional groups non reactive. This practice is well recognized in the art, see for example, Theodora Greene, *Protective Groups in Organic Synthesis*

(1991). Thus when reaction conditions are such that they can cause undesired reactions with other parts of the molecule, the skilled artisan will appreciate the need to protect these reactive regions of the molecule and act accordingly.

Starting materials used to prepare the compounds of Formula I are commercially available, known in the art, or prepared by known methods. Many of the preparations of starting materials herein are incorporated by reference from the patent literature.

Exemplary Disclosure

For the purpose of naming substituents in Formula I, the phenyl ring of any compound of formula I or intermediate used in its preparation shall be numbered;

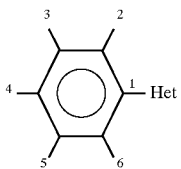

Thus when a compound of formula I has substitution on the phenyl ring, it is referred to by this numbering system regardless of how the compound is actually named. For example, if a compound is prepared and the designation is $R_1$, $R_2$=3,5-dimethyl, this means

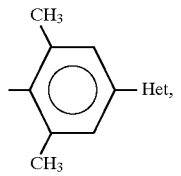

regardless of whether 3,5-dimethyl or 2,6-dimethyl appears the name of the compound.

For our purposes the same designations given for compounds of formula I are used for the intermediates. Thus a phenol intermediate may have $R_1$, $R_2$ and $R_3$ designated after the name of the product, and these designations have the same meanings as for the compound of formula I.

Preparation of Intermediates

Intermediate A

1-Amino-1-hydroxyiminoethane

A solution of 3.1 g of sodium in 60 ml of methanol (dissolved under nitrogen) was added dropwise to a stirred suspension of hydroxylamine hydrochloride (9.12 g) in 20 ml of methanol over a 15 min period. The reaction mixture was stirred at room temperature for 1.5 h, filtered, and the residual solids washed with 10 ml of methanol. To the combined filtrate was added 5.46 ml of acetonitrile, the resulting mixture was allowled to reflux for 24 h, and the solid precipitate was filtered. The filtrate was concentrated in vacuo to yield 4.61 g (46.1%) of 1-amino-1-hydroxyiminoethane as a white crystalline solid, m.p. 119°–122° C.

Intermediate B

3-[(3-Methyl-1,2,4-oxadiazol)-5-yl]propanol

To a mixture of 1-amino-1-hydroxyiminoethane (3 g, 40.5 mmol) and potassium carbonate (milled; 5.6 g) under nitrogen was added gamma-butyrolactone (3.17 g, 36.8 mmol) and the mixture was slowly heated to 125°–130° C. for 50 min. The above mixture was heated at 125° C. for 3.5 h while adding additional gamma-butyrolactone (2×320 mg ). The above mixture was cooled, diluted with 20 ml of chloroform with stirring, and the organic layer was decanted. To the above organic layer was added 5 g of magnesium sulfate and 10 ml of chloroform, the mixture was stirred, and the organic layer was decanted. The solids were washed with chloroform (3×10 ml), the combined organic layer was dried over magnesium sulfate, and concentrated in vacuo to yield 2.82 g of a clear oil. The clear oil was purified by passing through a silica gel pad (4.5×5 cm) with ethyl acetate to afford 2.41 g (46.1%) of 3-[(3-methyl-1,2,4-oxadiazol)-5-yl]propanol.

Intermediate C 1 (1,3-Dimethyl-2-phenylmethoxy-5-trimethylstannyl)-benzene.

To a solution of (1,3-dimethyl-2-phenylmethoxy)benzyl bromide (1.0 g; 3.4 mmol) in 15 ml of ether at −20° C. was added under nitrogen and with stirring 1.36 ml (3.4mmol) of n-butyllithium (nBuLi) and the mixture was allowed to warm to room temperature over a period of 30 min. To the above mixture cooled to −20° C. was added dropwise trimethyltin chloride (1.36 ml, 3.4 mmol) over a period of 3 min, and the mixture was allowed to warm to room temperature. To the resulting mixture was added saturated aqueous ammonium chloride solution, water, and ether. The organic layer was washed with brine, dried over magnesium sulfate, filtered, and the filtrate was concentrated in vacuo to yield a clear oil. The clear oil was purified through a reverse phase column (ether, 95% methanol) to afford 0.68 g (53.3%) of (1,3-dimethyl-2-phenylmethoxy-5-trimethylstannyl)benzene.

2 (1,3-Dimethyl-2-phenylmethoxy-5-fluoro) benzene

A mixture of 0.83 g (1.94 mmol) of (1,3-dimethyl-2-phenylmethoxy-5-trimethylstannyl)benzene, 0.22 ml (1.94 mmol) of (1-fluoro-4-iodo)benzene, and 42 mg (0.06 mmol) of $PdCl_2((C_6H_5)_3P)_2$ in 8 ml of DMF was heated at 90° C. with stirring overnight. The mixture was cooled to room temperature, diluted with ether, and filtered through a plug of Supercel. The organic layer was washed with water (50 ml), brine (50 ml), dried over magnesium sulfate, and concentrated in vacuo to yield a purple/brown solid. The solid dissolved in methylene chloride/hexane was purified by passing it through a dry flash column eluting with hexane (500 ml), 5% ethyl acetate in hexane (200 ml), 10% ethylacetate in hexane (200 ml), 20% ethyl acetate in hexane (300 ml), and hexane. The solid product was recrystallized from ethyl acetate to afford 224 mg (41%) of (1,3-dimethyl-2-phenylmethoxy-5-fluoro)benzene.

3 [2,6-Dimethyl-4(4-fluoro)phenyl]phenol

To a mixture of 350 mg of 10% Pd/C, 1 ml of water, 10 ml of methanol, and 224 mg (0.73 mmol) of (1,3-dimethyl-2-phenylmethoxy-5-fluoro)benzene was added 230 mg (3.65 mmol) of ammonium bicarbonate and the resulting reaction mixture was allowed to react at 60° C. for 15 min. The mixture was cooled, and diluted with ethyl acetate and water. The organic layer was washed with water and brine, dried over magnesium sulfate, and concentrated in vacuo to afford 150 mg (95%) of [2,6-dimethyl-4(4-fluoro)phenyl]phenol.

Preparation of Example compounds of Formula I

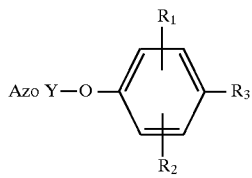

Formula I

EXAMPLE 1

1A 5-[4-(3-Cyano)propyloxy-3,5-dimethyl]phenyl-2-methyltetrazole(AZO-Y-=3-cyanopropyl, $R_1,R_2$=3,5-dimethyl, $R_3$=2-methyltetrazol-5-yl)

To a stirred solution of 5-[4-hydroxy-3,5-dimethyl]phenyl-2-methyltetrazole (15.52 g; 73.7 mmol) and 4-bromobutyronitrile (12 g; 81.1 mmol) in 200 ml of DMF under nitrogen was added 20.38 g (0.147 mol) of potassium carbonate and the resulting mixture was heated at 80° C. for 2 h. The above reaction mixture was cooled, diluted with 300 ml of water, and extracted with ether (3×300 ml). The organic layer was washed with water (4×100 ml), 10% NaOH solution, water (1×200 ml), and dried over magnesium sulfate. The organic layer was concentrated in vacuo, the residue was dissloved in 50 ml of methylene chloride and concentrated in vacuo to afford 19.3 g (86.8%) of 5-[4-(3-cyano)propyloxy-3,5-dimethyl]phenyl-2-methyl-tetrazole. The product was purified by LC column chromatography (900 g Keiselgel; 30% ethyl acetate in hexane) to afford 13.16 g of 5-[4-(3-cyano)propyloxy-3,5-dimethyl]phenyl-2-methyltetrazole as white crystalline solids.

1B 5-[4-[3-(Tetrazol-5-yl)propyloxy]-3,5-dimethyl]phenyl-2-methyltetrazole(AZO-Y-=3-(tetrazol-5-yl)propyl, $R_1,R_2$= 3,5-dimethyl, $R_3$=2-methyltetrazol-5-yl)

A solution of 7 g (26 mmol) of 5-[4-(3-cyano)propyloxy-3,5-dimethyl]phenyl-2-methyl-tetrazole, 5.03 g (77.4 mmol) of sodium azide, 5.37 g (39 mmol) of triethylamine hydrochloride in 75 ml of N-methyl-2-pyrrolidinone under nitrogen was heated at 150° C. with stirring overnight. To the mixture was added 22.2 g of sodium nitrite in 222 ml of deionized water and the resulting mixture was acidified carefully with 20% sulfuric acid solution to pH 4. The solid product was filtered, washed thoroughly with deionized water, and dried in vacuo. The mother liquor was refiltered and the combined solids dried in vacuo to afford 8.86 g (96%) of 5-[4-[3-(tetrazol-1-yl)propyloxy]-3,5-dimethyl]phenyl-2-methyl-tetrazole, as a light tan solid product, m.p. 175°–176° C.

1C 5-[4-(2-Methyltetrazol-5-yl)propyloxy-3,5-dimethyl]phenyl-2-methyl-tetrazole(AZO-Y-=3-(2-methyltetrazol-1-yl)propyl, $R_1,R_2$=3,5-dimethyl, $R_3$=2-methyltetrazol-5-yl)

To a solution of 7.3 g (23.2 mmol) of 5-[4-(3-tetrazol-5-yl)propyloxy-3,5-dimethyl]phenyl-2-methyltetrazole in 100 ml of N-methylpyrrolidone (NMP) under nitrogen with stirring was added 10.12 ml (58.1 mmol) of diisopropylethylamine. To the resulting mixture was added dropwise 1.81 ml (29 mmol) of iodomethane in 25 ml of NMP over a period of 15 min (the temperature rose to 29° C. during the addition) and the mixture was stirred at room temperature overnight. The mixture was diluted with 600 ml of water/NMP (5:1), extracted with ethyl acetate, and the organic layer was dried over magnesium sulfate and filtered through a plug of silica. The organic layer was concentrated in vacuo to yield 11.07 g of a crude product which was purified by flash column chromatography (300 g of Keiselfel; ethyl acetate/hexane, 1:1) and recrystallization from methanol to afford 2.99 g of 5-[4-(2-methyltetrazol-1-yl)propyloxy-3,5-dimethyl]phenyl-2-methyl-tetrazole, as a white crystalline solid, m.p. 112°–113° C., and 2.19 g of 5-[4-(1-methyltetrazol-5-yl)propyloxy-3,5-dimethyl]phenyl-2-methyl-tetrazole, as a white crystalline solid, m.p. 135°–136° C.

EXAMPLE 2

2A 4-[[2,6-Dimethyl-4-(2-methyl-tetrazol-5-yl)]phenyloxy]butyric amide(AZO-Y-=1-oxo-1-aminobutyl, $R_1,R_2$=2,6-dimethyl, $R_3$=2-methyltetrazol-5-yl)

A stirred solution of 5-[4-(3-cyano)propyloxy-3,5-dimethyl]phenyl-2-methyl-tetrazole(1 g; 3.7 mmol) and mercuric acetate (1.18 g; 3.7 mmol) in 100 ml of glacial acetic acid was allowed to reflux under nitrogen for 24 h. After adding 350 mg of mercuric acetate, the mixture was allowed to reflux for an additional 48 h. The reaction mixture was cooled, poured over 150 ml of ice/water, and the mixture was extracted with methylene chloride (5×75 ml). The organic layer was washed with dilute sodium bicarbonate solution (2×200 ml), water, brine, and dried over magnesium sulfate. The organic solution was concentrated in vacuo to afford 1.08 g (theory) of 4-[[2,6-dimethyl-4-(2-methyltetrazol-5-yl)]phenyloxy]butyric amide, as a pale yellow solid.

2B 5-[(3,5-Dimethyl)-4-[4-oxo-4-(1-dimethylaminoethyleneamino]-butyloxy]phenyl-2-methyltetrazole(AZO-Y-=4-oxo-4-(1-dimethyl-aminoethyleneamino)-butyl, $R_1,R_2$=3,5-dimethyl, $R_3$=2-methyltetrazol-5-yl)

A mixture of 1.0 g of 4-[[2,6-dimethyl-4-(2-methyltetrazol-5-yl)]phenyloxy]-butyric amide and 2.0 ml of N,N-dimethylacetamide dimethyl acetal under nitrogen was heated with stirring at 150° C. for 4 h. The excess acetal was removed in vacuo and 1.3 g of 5-[(3,5-dimethyl)-4-[4-oxo-4-(1-dimethyl-aminoethylene)amino]butyloxy]phenyl-2-methyltetrazole was isolated as a red oil (a crude oil) which was used without further purification.

2C 5-[4-(3-Methyl-1,2,4-oxadiazol-5-yl)propyloxy-3,5-dimethyl]phenyl-2-methyl-tetrazole(AZO-Y-=3-methyl-1,2,4-oxadiazol-5-yl)propyl, $R_1,R_2$=3,5-dimethyl, $R_3$=2-methyltetrazol-5-yl)

To a solution of sodium hydroxide (176 mg), 0.89 ml of distilled water, 310 mg (4.4 mmol) of hydroxylamine hydrochloride, and 4.2 ml of p-dioxane in 8.5 ml of 70% of acetic acid/water placed in 50 ml of flask equiped with a drying tube was added 1.3 g (3.6 mmol) of 5-[(3,5-dimethyl)-4-[4-oxo-4-(1-dimethylaminoethylene)amino]butyloxy] phenyl-2-methyltetrazole and the mixture was heated at 90° C. for 4h. To the reaction mixture was added 30 ml of water and 30 ml of chloroform, and the aqueous layer was extracted with chloroform (3×15 ml). The combined organic layer was dried over magnesium sulfate, filtered, and passed through a silica gel pad. The organic solution was concentrated in vacuo to yield 1.0 g of a crude yellow oil which was purified by a flash column chromatography (100 g of Keisel gel; 40% ethyl acetate/hexane) followed by recrystallization from methanol to afford 492 mg of 5-[4-(3-methyl-1,2,4-oxadiazol-5-yl)propyloxy-3,5-dimethyl]phenyl-2-methyl-tetrazole (VOKB-86-A; WIN 62002, from fraction A-C) as a white solid, m.p. 87.5–88.5° C. and 665 mg of 5-[4-(3-methoxycarbonyl)propyloxy-3,5-dimethyl]phenyl-2-methyltetrazole as a white solid, m.p. 107.5°–108° C.

EXAMPLE 3

A. 3-[4-(3-Methyl-1,2,4-oxadiazol-5-yl)propyloxy-3,5-dimethyl]phenyl-5-methyl-1,2,4-oxadiazole(AZO-Y-=3-methyl-1,2,4-oxadiazol-5-yl)propyl, $R_1,R_2$=3,5-dimethyl, $R_3$=5-methyl-1,2,4-oxadiazol-3-yl)

To a mixture of 540 mg (38.07 mmol) of 3-[(3-methyl-1,2,4-oxadiazol)-5-yl]propanol, 860 mg (41.87 mmol) of 5-methyl-3-[4-hydroxy-3,5-dimethyl]-phenyl-1,2,4-oxadiazole, and 1.1 g of triphenylphosphine in 5 ml of THF under nitrogen, which was stirred and chilled to 0° C., was added 730 mg (1.1 eq) of diethyl azodicarboxylate (DEAD) in 5 ml of THF over a period of 5 min. The reaction mixture was stirred at room temperature for 1.5 h, diluted with water, and extracted with ether (2×). The organic layer was washed with 10% sodium hydroxide solution, water, brine, and dried over magnesium sulfate. The organic solution was diluted with hexane (equal volume) and concentrated in vacuo to yield 1.48 g of a white solid which was purified by flash column chromatography (silica gel; 2.5×11 cm, 40% ethyl acetate in hexane) to afford 1.11 g (88.8%) of 3-[4-(3-methyl-1,2,4-oxadiazol-5-yl)propyloxy-3,5-dimethyl] phenyl-5-methyl-1,2,4-oxadiazole, as a white solid, m.p.88°–89° C. (recrystallized from methanol and dried in vacuo).

EXAMPLE 4

3-[4-(3-Methyl-1,2,4-oxadiazol-5-yl)propyloxy-3,5-dimethyl]phenyl-5-trifluoromethyl-1,2,4-oxadiazole (AZO-Y-=3-methyl-1,2,4-oxadiazol-5-yl)propyl, $R_1$, $R_2$=3,5-dimethyl, $R_3$=5-trifluoro-methyl-1,2,4-oxadiazol-3-yl)

To a mixture of 460 mg (32.69 mmol) of 3-(3-methyl-1,2,4-oxadiazol-5-yl)propanol, 930 mg (35.96 mmol) of 5-trifluoromethyl-3-[4-hydroxy-3,5-dimethyl]phenyl-1,2,4-oxadiazole, and 940 mg of tripenylphosphine in 5 ml of THF under nitrogen, which was stirred and chilled to 0° C., was added 630 mg (1.1 eq) of diethyl azodicarboxylate (DEAD) in 5 ml of THF over a period of 5 min. The reaction mixture was stirred at room temperature for 1.5 h, diluted with water, and extracted with ether (3×). The oraganic layer was washed with 2% sodium hydroxide solution, water, brine, and dried over magnesium sulfate. The organic solution was concentrated in vacuo to yield 2.28 g of a white solid which was purified by flash column chromatography (silica gel; 1.5×9 cm, 20% ethyl acetate in hexane) to afford 1.04 g (83.2%) of 3-[4-(3-methyl-1,2,4-oxadiazol-5-yl)propyloxy-3,5-dimethyl]phenyl-5-trifluoromethyl-1,2,5-oxadiazole, as a yellow oil. The oil was crystallized from hot methanol and dried in vacuo to afford 638 mg of a solid product, m.p. 79°–80° C.

EXAMPLE 5

A. 5-[4-(3-Ethoxycarbonyl)propyloxy-3,5-dimethyl] phenyl-2-methyl-tetrazole(AZO-Y-=3-(ethoxycarbonyl)propyl, $R_1,R_2$=3,5-dimethyl, $R_3$=2-methyltetrazol-5-yl)

A mixture of 5-[4-hydroxy-3,5-dimethyl]phenyl-2-methyltetrazole (10.21 g; 50 mmol), ethyl 4-bromobutyrate (8 ml; 55 mmol), 6.9 g (50 mmol) of potassium carbonate, and 8.25 g (55 mmol) of sodium iodide in 100 ml of acetonitrile was allowed to reflux under nitrogen for 43 h. The reaction mixture was concentrated in vacuo, the residue was stirred with 10% NaOH solution, and the resulting mixture was filtered. The residual solid and the filtered brown oil were triturated with methylene chloride, the organic layer was washed with water, brine, and dried over magnesium sulfate. The organic layer was concentrated in vacuo, the residual oil was triturated with methanol and concentrated in vacuo. The above residue was purified by passing through a plug of silica gel with methylene chloride followed by concentration in vacuo to afford 5.38 g (34%) of 5-[4-(3-ethoxycarbonyl)propyloxy-3,5-dimethyl]phenyl-2-methyl-tetrazole, as a yellow oil.

B. 5-[4-(3-Carboxy)propyloxy-3,5-dimethyl]phenyl-2-methyl-tetrazole(AZO-Y-=3-(carboxy)propyl, $R_1,R_2$=3,5-dimethyl, $R_3$=2-methyltetrazol-5-yl)

A mixture of 5-[4-(3-ethoxycarbonyl)propyloxy-3,5-dimethyl]phenyl-2-methyl-tetrazole (5.38 g; 17 mmol), lithium hydroxide (0.46 g; 19 mmol) in 50 ml of methanol and 5 ml of water with stirring and under nitrogen was allowed to reflux for 30 min. The mixture was cooled to room temperature, concentrated in vacuo, the residue was treated with water, and the resulting mixture was extracted with ether. The aqueous layer was acidified with conc. HCl solution with stirring, filtered, and the solid product (5.02 g) was dried in vacuo and recrystallized from propyl acetate to afford 3.75 g (76%) of 5-[4-(3-carboxy)propyloxy-3,5-dimethyl]phenyl-2-methyl-tetrazole, as a white solid, m.p. 120°–121° C.

C. 5-[4-(3-Propargylaminocarbonyl)propyloxy-3,5-dimethyl]phenyl-2-methyl-tetrazole(AZO-Y-=3-(propargylamino-carbonyl)propyl, $R_1,R_2$=3,5-dimethyl, $R_3$=2-methyltetrazol-5-yl)

A mixture of 5-[4-(3-carboxy)propyloxy-3,5-dimethyl] phenyl-2-methyl-tetrazole (2.94 g; 10 mmol) and carbonyl diimidazole (1.95 g; 12 mmol) in 50 ml of methylene chloride under nitrogen was refluxed with stirring for 15 min. The mixture was cooled, 1 ml (15 mmol) of propargylamine was added in one portion, and the resulting reaction mixture was stirred for 1 h at room temperature. The reaction mixture was quenched with 3N HCl solution with stirring, the organic layer was washed with water, brine, and dried over magnesium sulfate. The organic solution was concentrated in vacuo and the residual solid (3.38 g; m.p. 126°–128° C.) was recrystallized from methanol to afford 2.47 g (74%) of 5-[4-(3-propargylaminocarbonyl) propyloxy-3,5-dimethyl]phenyl-2-methyl-tetrazole as a white crystalline solid, m.p. 129°–130° C.

D. 5-[4-(5-Methyl-oxazol-2-yl)propyloxy-3,5-dimethyl] phenyl-2-methyl-tetrazole(AZO-Y-=5-methyloxazol-2-yl) propyl, $R_1,R_2$=3,5-dimethyl, $R_3$=2-methyltetrazol-5-yl)

A mixture of 5-[4-(3-propargylaminocarbonyl) propyloxy-3,5-dimethyl]phenyl-2-methyl-tetrazole (980 mg; 3 mmol) and mercuric acetate (50 mg; 0.16 mmol) in 10 ml of glacial acetic acid was allowed to reflux for 5 h with stirring and under nitrogen and then cooled to room temperature. The mixture was concentrated in vacuo, the residue was dissolved in methylene chloride, and the organic layer was washed with 10% potassium carbonate, water, brine, and dried over magnesium sulfate. The organic layer was concentrated in vacuo and the residual yellow oil (880 mg) was passed through a silica gel plug (with ether) to yield 660 mg of a white oil which was purified by MPLC chromatography (silica gel, hexane/ethyl acetate, 1:1) to afford 530 mg (54%) of 5-[4-(5-methyl-oxazol-2-yl)propyloxy-3,5-dimethyl]phenyl-2-methyl-tetrazole as a colorless oil. The oil was crystallized from methanol and recrystallized from acetonitrile to yield white crystalline solids, m.p. 80°–81° C.

EXAMPLE 6

A. 5-([4-(3-Ethoxycarbonyl)propyloxy-3,5-dimethyl] phenyl)-2-methyl-tetrazole(AZO-Y-=3-(ethoxycarbonyl) propyl, $R_1,R_2$=3,5-dimethyl, $R_3$=2-methyltetrazol-5-yl)

A mixture of 5-([4-hydroxy-3,5-dimethyl]phenyl)-2-methyltetrazole (10.21 g; 50 mmol), ethyl 4-bromobutyrate (10 ml; 70 mmol), 13.8 g (100 mmol) of potassium carbonate, and 11.6 g (70 mmol) of sodium iodide in 200 ml of acetonitrile was allowed to reflux under nitrogen for 17 h. The reaction mixture was concentrated in vacuo, the residue was stirred with ethyl acetate, filtered, and the filtrate was washed with 10% NaOH solution, water, and brine. The organic layer was dried over magnesium sulfate, filtered, and concentrated in vacuo to afford 17.49 g of 5-[4-(3-ethoxycarbonyl)propyloxy-3,5-dimethyl]phenyl-2-methyltetrazole, as a brown oil.

B. 5-[4-(3-Carboxy)propyloxy-3,5-dimethyl]phenyl-2-methyl-tetrazole(AZO-Y-=3-(carboxy)propyl, $R_1,R_2$=3,5-dimethyl, $R_3$=2-methyltetrazol-5-yl)

A mixture of 5-[4-(3-ethoxycarbonyl)propyloxy-3,5-dimethyl]phenyl-2-methyl-tetrazole (15.9 g; 50 mmol), lithium hydroxide (1.2 g; 50 mmol) in 100 ml of methanol and 10 ml of water with stirring and under nitrogen was allowed to reflux for 1 h. After adding an additional lithium hydroxide (5 equiv), the mixture was refluxed for additional 4 h, cooled to room temperature, and concentrated in vacuo. The residue was treated with water and charcoal, and the resulting mixture was filtered. The aqueous layer was acidified with conc. HCl solution with stirring, filtered, and the solid product (12.27 g; 91%) was dried in vacuo to afford 5-[4-(3-carboxy)propyloxy-3,5-dimethyl]phenyl-2-methyl-tetrazole, as white solids, m.p. 118°–119.5° C.

C. 4-[4-(2-Methyl-tetrazol-5-yl)-2,6-dimethylphenyloxy]butanoyl chloride(AZO-Y-=3-(chlorocarbonyl)propyl, $R_1,R_2$=3,5-dimethyl, $R_3$=2-methyltetrazol-5-yl)

A mixture of 5-[4-(3-carboxy)propyloxy-3,5-dimethyl]phenyl-2-methyl-tetrazole (5.81 g; 20 mmol), 20 ml of thionyl chloride, and 4 drops of DMF was stirred at room temperature under nitrogen for 48 h. The mixture was concentrated in vacuo to afford 6.88 g of 4-[4-(2-methyltetrazol-5-yl)-2,6-dimethylphenyloxy]butanoyl chloride, as a tan solid.

D. 5-[4-(4-Oxo-4-diazomethyl)butyloxy-3,5-dimethyl]phenyl-2-methyl-tetrazole(AZO-Y-=4-oxo-4-diazomethylbutyl, $R_1,R_2$=3,5-dimethyl, $R_3$=2-methyltetrazol-5-yl)

A solution of Diazald (11.93 g;56mmol) dissolved in 110 ml of ether was filtered into a dropping funnel. This solution was added dropwise (approx 4 drops/min) to a stirred solution of KOH (2.8 g) in 20 ml of ethanol/water (3:1) warmed at 65° C. To the resulting mixture was added a solution of 4-[4-(2-methyl-tetrazol-5-yl)-2,6-dimethylphenyloxy]butanoyl chloride (20 mmol) in ethanol/methylene choride at 0° C. with stirring over a period of 35 min. Ether (25 ml) was added dropwise through a dropping funnel at 0° C. and the mixture was allowed to warm to room temperature gradually. After bubbling nitrogen through, the mixture was concentrated in vacuo to yield 6.84 g of a yellow solid. The solid was purified by silica gel column chromatography (hexane/ethyl acetate, 1:1) to afford 3.83 g (60.8%) of 5-[4-(4-oxo-4-diazomethyl)butyloxy-3,5-dimethyl]phenyl-2-methyltetrazole, as a yellow solid.

E. 5-[4-(2-Methyl-oxazol-5-yl)propyloxy-3,5-dimethyl]phenyl-2-methyl-tetrazole(AZO-Y-=2-methyloxazol-5-yl)propyl, $R_1,R_2$=3,5-dimethyl, $R_3$=3-methyltetrazol-1-yl)

A solution of 1-[4-(4-oxo-4-diazomethyl)butyloxy-3,5-dimethyl]phenyl-3-methyl-tetrazole (1.4 g; 4.45 mmol) in 20 ml of acetonitrile was added dropwise to boron trifluorideetherate in 40 ml of acetonitrile under nitrogen with stirring in an ice-bath over a period of 35 min. The mixture was warmed to room temperature, stirred overnight, and then poured into 10% NaOH solution. To the above mixture was added ether, and the organic layer was washed with water, brine, and dried over magnesium sulfate. The organic layer was concentrated in vacuo and the residual yellow oil (1.36 g) was purified by passing through a silica gel column with ethyl acetate to afford 0.72 g (49%) of 5-[4-(2-methyl-oxazol-5-yl)propyloxy-3,5-dimethyl]phenyl-2-methyl-tetrazole, as a white solid, m.p. 67°–68° C. (recrystallization from triethylamine).

EXAMPLE 7

A. 4-[4-(2-Methyl-tetrazol-5-yl)-2,6-dimethylphenyloxy]butanamide(AZO-Y-=4-oxo-4-amino)butyl, $R_1,R_2$=3,5-dimethyl, $R_3$=2-methyltetrazol-5-yl)

A mixture of 5-[4-(3-Carboxy)propyloxy-3,5-dimethyl]phenyl-2-methyl-tetrazole (2.9 g; 10 mmol) and carbonyl diimidazole (1.95 g; 12 mmol) in 50 ml of THF under nitrogen was allowed to reflux for 5 h with stirring. The mixture was cooled to room temperature, chilled in an ice-bath, and 5 ml of 30% ammonium hydroxide was added in one portion, and the resulting mixture was allowed to react with stirring at room temperature overnight. The mixture was concentrated in vacuo, the residue was triturated in water and filtered to afford 2.72 g (94%) of 4-[4-(2-methyl-tetrazol-5-yl)-2,6-dimethylphenyloxy]-butanamide, as a white solid, m.p.155°–156° C.

B. 5-[4-(4-Chloromethyl-oxazol-2-yl)propyloxy-3,5-dimethyl]phenyl-2-methyl-tetrazole(AZO-Y-=4-chloromethyl-oxazol-2-yl)propyl, $R_1,R_2$=3,5-dimethyl, $R_3$=2-methyltetrazol-5-yl)

A mixture of 4-[4-(2-methyl-tetrazol-5-yl)-2,6-dimethylphenyloxy]-butanamide (530 mg; 1.83 mmol) and 1,3-dichloroacetone (600 mg; 4.73 mmol) in 25 ml of toluene was allowed to reflux with stirring under nitrogen for 16 h. The reaction mixture was filtered through a plug of silica gel eluting with hexane/ethyl acetate (6:4) and 370 mg of a yellow oil was obtained. The oil was purified by chromatography (HPLC; hexane/ethyl acetate, from 7:3 to 6:4) to afford 304 mg (14%) of 5-[4-(4-chloromethyl-oxazol-2-yl)propyloxy-3,5-dimethyl]phenyl-2-methyl-tetrazole, as an oil.

C. 5-[4-(4-Chloromethyl-oxazol-2-yl)propyloxy-3,5-dimethyl]phenyl-2-methyl-tetrazole(AZO-Y-=4-chloromethyl-oxazol-2-yl)propyl, $R_1,R_2$=3,5-dimethyl, $R_3$=2-methyltetrazol-5-yl)

A mixture of 4-[4-(2-methyl-tetrazol-5-yl)-2,6-dimethylphenyloxy]-butanamide (1.75 g; 6.05 mmol) and 1,3-dichloroacetone (1.26 g; 9.9 mmol) in 50 ml of toluene, placed in a flask equipped with a Dean-Stark trap, was allowed to reflux with stirring under nitrogen for 16 h. After adding additional 1,3-dichloroacetone (530 mg; 4.2 mmol), the mixture was allowed to reflux overnight. The reaction mixture was cooled and concentrated in vacuo and the residue was purified by chromatography (HPLC; hexane/ethyl acetate,6:4; ethyl acetate, and 10% propanol in ethyl acetate) to afford 5-[4-(4-chloromethyl-oxazol-2-yl)propyloxy-3,5-dimethyl]phenyl-2-methyl-tetrazole (1.53 g; theory), as an oil.

D. 5-[4-(4-Methyl-oxazol-2-yl)propyloxy-3,5-dimethyl]phenyl-2-methyl-tetrazole(AZO-Y-=4-methyloxazol-2-yl)propyl, $R_1,R_2$=3,5-dimethyl, $R_3$=2-methyltetrazol-5-yl)

A mixture of 5-[4-(4-chloromethyl-oxazol-2-yl)propyloxy-3,5-dimethyl]phenyl-2-methyl-tetrazole (160 mg; 0.44 mmol) and lithium aluminum hydride (5 equiv) in 15 ml of THF was allowed to reflux under nitrogen with stirring for 15 min, cooled, and quenched with saturated ammonium chloride solution. The above mixture was filtered through supercel and purified by chromatography (silica gel; methylene chloride/ethyl acetate, 1:1) to afford 76 mg (32%) of 5-[4-(4-methyl-oxazol-2-yl)propyloxy-3,5-dimethyl]phenyl-2-methyl-tetrazole as a white crystalline solid, m.p. 110°–112° C.

EXAMPLE 8

A. 5-[4-(3-Bromo)propyloxy-3,5-dimethyl]phenyl-2-methyltetrazole(AZO-Y-=3-bromopropyl, $R_1,R_2$=3,5-dimethyl, $R_3$=2-methyltetrazol-5-yl)

To a mixture of 2.78 g (20 mmol) of 3-bromopropanol, 4.9 g (24 mmol) of 5-[4-hydroxy-3,5-dimethyl]phenyl-2-methyltetrazole, and 3.78 ml (24 mmol) of diethyl azodicarboxylate (DEAD) in 50 ml of THF(dry) was added dropwise at 0° C. 6.29 g (24 mmol) of tripenylphosphine in 100 ml of THF(dry) under nitrogen over a period of 1 h. The mixture was partitioned between 500 ml of water and 100 ml of ether. The aqueous layer was extracted with 100 ml of ether, the combined organic layer was washed with 10% sodium hydroxide solution, brine, and dried over magnesium sulfate. The organic solution was concentrated in vacuo to yield 13.8 g of a brown oil which was purified by flash column chromatography (Keiselgel 60; 50×460 mm, 20% ethyl acetate in hexane) to afford 5.38 g (82%) of 5-[4-(3-bromo)propyloxy-3,5-dimethyl]phenyl-2-methyl-tetrazole, as a white solid.

B. 5-[4-[3-(Imidazol-1-yl)propyloxy]-3,5-dimethyl]phenyl-2-methyl-tetrazole(AZO-Y-=-(3-imidazol-1-yl)propyl, $R_1,R_2$=3,5-dimethyl, $R_3$=2-methyltetrazol-5-yl)

A mixture of 2.6 g (8 mmol) of 5-[4-(3-bromo)propyloxy-3,5-dimethyl]phenyl-2-methyl-tetrazole, 1.09 g (10 mmol) of imidazole, 2.76 g (20 mmol) of potassium carbonate, and 130 mg (0.8 mmol) of potassium iodide in 35 ml of N-methyl-2-pyrrolidinone under nitrogen was allowed to react at 60°–70° C. with stirring for 4 h. The reaction mixture was cooled and 200 ml of water, 100 ml of brine, and 75 ml of ether were added. The aqueous layer was extracted with ether (3×50 ml) and the combined organic layer was washed with water and brine. The organic layer was extracted with 1N HCl solution (3×50 ml) and the acidic solution was basified with 1N NaOH solution (to pH=8). The above mixture was extracted with methylene chloride (3×30 ml), the organic layer dried over magnesium sulfate, and concentrated in vacuo to yield 2.09 g of a yellow oil. The oil which was purified by flash column chromatography (2×; 120 g Keisel gel 60; 10% isopropanol in chloroform, 5% isopropanol in chloroform ) to afford 1.57 g of 5-[4-[3-(imidazol-1-yl)propyloxy]-3,5-dimethyl]phenyl-2-methyltetrazole as a white crystalline solid, m.p. 92.5°–94° C. (from ether).

C. 5-[4-[3-(2-Methyl)imidazol-1-yl]propyloxy-3,5-dimethyl]phenyl-2-methyl-tetrazole(AZO-Y-=3-(2-methylimidazol-1-yl)propyl, $R_1,R_2$=3,5-dimethyl, $R_3$=2-methyltetrazol-5-yl)

A mixture of 2.94 g (9 mmol) of 5-[4-(3-bromo) propyloxy-3,5-dimethyl]phenyl-2-methyl-tetrazole, 1.72 g (20 mmol) of 2-methylimidazole, 3.63 g (21 mmol) of potassium carbonate, and 170 mg (1 mmol) of potassium iodide in 35 ml of N-methyl-2-pyrrolidinone under nitrogen was allowed to react at 60°–70° C. with stirring overnight. The reaction mixture was cooled and 200 ml of water, 100 ml of brine, and 75 ml of ether were added. The aqueous layer was extracted with ether (3×50 ml) and the combined organic layer was washed with water and brine. The organic layer was extracted with 1N HCl solution (3×50 ml) and the acidic solution was basified with 1N NaOH solution (to pH=8). The above mixture was extracted with methylene chloride (3×30 ml), the organic layer dried over magnesium sulfate, and concentrated in vacuo to yield 2.67 g of a solid. The solid product was purified by flash column chromatography (2×; 120 g Keisel gel 60; 2.5% isopropanol in chloroform) to afford 1.77 g of 5-[4-[3-(2-methyl)imidazol-1-yl]propyloxy-3,5-dimethyl]phenyl-2-methyl-tetrazole as a white crystalline solid, m.p. 121°–122.5° C. (from ether).

D. 5-[4-[3-(4-Methyl)imidazol-1-yl]propyloxy-3,5-dimethyl]phenyl-2-methyl-tetrazole(AZO-Y-=3-(4-methylimidazol-1-yl)propyl, $R_1,R_2$=3,5-dimethyl, $R_3$=2-methyltetrazol-5-yl)

A mixture of 3.6 g (11 mmol) of 5-[4-(3-bromo) propyloxy-3,5-dimethyl]phenyl-2-methyl-tetrazole, 1.09 g (10 mmol) of 4-methylimidazole, 3.87 g (28 mmol) of potassium carbonate, and 190 mg (11 mmol) of potassium iodide in 35 ml of N-methyl-2-pyrrolidinone under nitrogen was allowed to react at 60°–70° C. with stirring overnight. The reaction mixture was cooled and 200 ml of water, 100 ml of brine, and 50 ml of ether were added. The aqueous layer was extracted with ether (3×50 ml) and the combined organic layer was washed with water/brine(2×50 ml;1:1). The organic layer was extracted with 1N HCl solution (3×50 ml) and the acidic solution was basified with 1N NaOH solution (to pH=8.5) The above mixture was extracted with methylene chloride (3×30 ml), the organic layer dried over magnesium sulfate, and concentrated in vacuo to yield 2.92 g 67.3% of a yellow oil. The oil was purified by flash column chromatography (580 g Keiselgel 60; 1% isopropanol in chloroform). The combined fractions (fr 213–432) was concentrated in vacuo to yield 2.43 g of a yellow oil which was purified by successive fractional crystallizations from ether/methylene chloride to afford 340 mg of 5-[4-[3-(4-methyl)imidazol-1-yl]propyloxy-3,5-dimethyl]phenyl-2-methyl-tetrazole as a pale yellow crystalline solid, m.p. 126°–127° C.

EXAMPLE 9

A. 2-[4-[4-(2-Methyl-tetrazol-5-yl)-2,6-dimethylphenoxy]-1-hydroxy-butyl]-1-methylimidazole To a cold solution of 1-methylimidazole (164 mg, 2 mmol) in 20 ml of THF was added at –30° C. n-BuLi (2.5M in hexane, 0.8 ml, 2 mmol). The mixture was stirred at –30°–40° C. for 1 h and then cooled to –50° C. To the above mixture was added dropwise at –50° C. a solution of 4-[(2-methyl-tetrazol-5-yl)-2,6-dimethylphenoxy]-butylcarboxaldehyde (548 mg, 2 mmol) in 10 ml of THF, and the mixture was stirred at –40°–50° C. for 1 h and then allowed to warm to 20° C. An aqueous ammonium chloride solution was added to the mixture, and the resulting reaction mixture was extracted with methylene chloride. The organic layer was dried over sodium sulfate and concentrated in vacuo. The residue was purified by silica column chromatography (20 cm column, methylene chloride/methanol, 30/1-10/1) followed by recrystallization from hot acetonitrile/ether to afford 425 mg (60%) of 2-[4-[4-(2-methyl-tetrazol-5-yl)-2,6-dimethylphenoxy]-1-hydroxy-butyl]-1-methylimidazole, as a white crystalline solid, m.p.151°–154° C.

B. 2-[4-[4-(2-Methyl-tetrazol-5-yl)-2,6-dimethylphenoxy]-1-phenoxythiocarbonyloxy-butyl]-1-methylimidazole To a solution of 2-[4-[4-(2-methyl-tetrazol-5-yl)-2,6-dimethylphenoxy]-1-hydroxy-butyl]-1-methylimidazole (690 mg, 1.94 mmol) in 30 ml of acetonitrile was added at 20° C. 473 mg (3.88 mmol) of DMAP and 403 mg (2.33 mmol) of phenyl chlorothioformate, and the mixture was stirred at 20° C. for 3 h. The solvent was concentrated in vacuo and the residue was partitioned between methylene chloride and an aqueous sodium bicarbonate solution. The organic layer was dried over sodium sulfate and concentrated in vacuo. The residue was purified by silica column chromatography (20 cm column, ethyl acetate/hexane, 1/1-4/1) to afford 750 mg (78%) of 2-[4-[4-(2-methyl-tetrazol-5-yl)-2,6-dimethylphenoxy]-1-phenoxythiocarbonyloxy-butyl]-1-methylimidazole, as a yellow oil.

C. 2-[4-[4-(2-Methyl-tetrazol-5-yl)-2,6-dimethylphenoxy]-butyl]-1methylimidazole (I, Azo=1-methyl-2-imidazolyl, n=4, $R_1,R_2$=3,5-dimethyl, $R_3$=2-methyl-tetrazol-5-yl)

To a solution of 2-[4-[4-(2-methyl-tetrazol-5-yl)-2,6-dimethylphenoxy]-1-phenoxythiocarbonyloxy-butyl]-1-methylimidazole (1.94 mmol) in 35 ml of toluene was added AIBN (159 mg, 0.97 mmol) and n-tributyltin hydride (1.69 g), and the mixture was stirred at 75°–80° C. for 4 h. An aqueous sodium bicarbonate solution was added to the mixture, and the mixture was extracted with ethyl acetate, and then methylene chloride (2×). The combined organic layer was dried over sodium sulfate and concentrated in vacuo. The residue was purified by silica column chromatography (20 cm column, methylene chloride/methanol, 30/1-15/1) to afford 440 mg (67%) of 2-[4-[4-(2-methyltetrazol-5-yl)-2,6-dimethylphenoxy]-butyl]-1-methylimidazole, m.p. 100°–102° C. (from methylene chloride/hexane).

EXAMPLE 10

A. 2-Ethyl-1-methyl-5-tributyltin-imidazole

To a solution of 2-ethyl-1-methyl-5-imidazole (3.79 g, 34.5 mmol) in 120 ml of ether was added 14.2 ml (35.5 mmol) of 2.5M butyllithium dropwise at 20° C. The resulting mixture was stirred for 4 h, and then 11.78 g (36.2 mmol) of tributyltin chloride was added dropwise. The suspension was stirred overnight and an aqueous ammonium chloride solution was added. The organic layer was washed with brine, dried over sodium sulfate, and concentrated in vacuo to afford 6.78 g (17.2 mmol, 49.8%) of 2-ethyl-1-methyl-5-tributyltin-imidazole.

B. Ethyl β-(2-ethyl-1-methyl-imidazol-5-yl)acrylate

To a solution of 2-ethyl-1-methyl-5-tributyltin-imidazole (17.2 mmol) in 130 ml of xylene was added 4.28 g (18.9 mmol) of ethyl β-(iodo)acrylate followed by Pd(PPh$_3$)$_4$ (993 mg, 0.86 mmol). The mixture was heated at 120° C. for 18 h under nitrogen, cooled, and water was added. The organic layer was separated and washed with 10% ammonium hydroxide solution, and brine. The aqueous mixture was extracted with ethyl acetate, and the combined organic layer was dried over sodium sulfate and concentrated in vacuo. The residue was purified by silica chromatography (20 cm silica column, ethyl acetate/hexane 1/1-2/1; methylene chloride/methanol 50/1-30/1) to yield 2.43 g (68%) of ethyl β-(2-ethyl-1-methyl-imidazol-5-yl)acrylate.

C. Ethyl 3-(1-methyl-2-ethyl-imidazol-5-yl)propionate

A mixture of ethyl β-(1-methyl-2-ethyl-imidazol-5-yl)acrylate (2.1 g, 10.1 mmol) and 1.1 g of 10% Pd/C in ethyl acetate/ethanol/HCl (1M in ethyl acetate; 50 ml/8 ml/8 ml) was hydrogenated under hydrogen (50 psi) for 2 h. The mixture was filtered through celite, the residue was washed with ethylene chloride/methanol (5:1, 2×), and the combined organic layer was concentrated in vacuo. The residue was basified with aqueous sodium bicarbonate solution, extracted with methylene chloride (4×), and the combined organic layer was dried over sodium sulfate and concentrated in vacuo. Upon chromatographic purification of the residue on 20 cm silica column (methylene chloride/methanol 50/1-15/1), 1.9 g (90%) of ethyl 3-(1-methyl-2-ethyl-imidazol-5-yl)propionate was isolated as a yellow oil.

D. 5-(3-Hydroxypropyl)-1-methyl-2-ethylimidazole

To a cooled (0° C.) solution of ethyl 3-(1-methyl-2-ethylimidazol-5-yl)propionate (1.75 g, 8:33 mmol) in 30 ml of THF was added 4.6 ml (4.6 mmol) of 1M LAH solution in THF at 0° C. After stirring at 0° C. for 15 min, the mixture was allowed to warm and stirred at 20° C. for 0.7 h. Rochelle salt solution (equiv) was added and the mixture was stirred for 20 min. The aqueous mixture was extracted with methylene chloride and filtered. The organic layer was dried over sodium sulfate and concentrated in vacuo. The residue was purified by chromatography on silica (10 cm column, methylene chloride/methanol, 6/1-6/1) followed by recrystallization from acetonitrile/ether and methylene chloride/hexane to afford 1.268 g (90%) of 5-(3-hydroxypropyl)-1-methyl-2-ethylimidazole, as a white solid, m.p. 69°–71° C.

E. 5-[3-[4-(2-Methyl-tetrazol-5-yl)-2,6-dimethylphenoxy]propyl]-1-methyl-2-ethylimidazole (I, Azo=1-methyl-2-ethylimidazol-5-yl, Y=1,3-propylene, R$_1$,R$_2$=3,5-dimethyl, R$_3$=2-methyl-tetrazol-5-yl)

A mixture of 5-(3-hydroxypropyl)-1-methyl-2-ethylimidazole (150 mg, 0.89 mmol), 4-(2-methyl-tetrazol-5-yl)-2,6-dimethylphenol (200 mg, 0.98 mmol), and triphenylphosphine (257 mg, 0.98 mmol) was dissolved in 10 ml of THF under nitrogen at 0° C. To the above solution was added at 0° C. DEAD (170.5 mg, 0.98 mmol) and the mixture was stirred for 30 2 h allowing the mixture to warm to 20° C. The solvent was removed in vacuo, and the residue was purified by silica column chromatography (20 cm column, ethyl acetate/hexane, 1/1-3/1; methylene chloride/methanol 30/1-10/1) to afford 376 mg (quantitative) of 5-[3-[4-(2-methyl-tetrazol-5-yl)-2,6-dimethylphenoxy]-propyl]-1-methyl-2-ethyl-imidazole, as a white crystalline solid, m.p. 96°–98° C. (recrystallization from methylene chloride/hexane).

F. 5-[3-[4-(2-Methyl-tetrazol-5-yl)phenoxy]-propyl]-1-methyl-2-ethylimidazole (I, Azo=1-methyl-2-ethylimidazol-4-yl, Y=1,3-propylene, R$_3$=(2-methyltetrazol-5-yl), R$_1$=R$_2$=hydrogen)

A mixture of 5-(3-hydroxypropyl)-1-methyl-2-ethylimidazole (150 mg, 0.89 mmol), 4-(2-methyl-tetrazol-5-yl)-phenol (172 mg, 0.98 mmol), and DEAD (171 mg, 0.98 mmol) was dissolved in 10 ml of THF under nitrogen at 0° C. To the above solution was added triphenylphosphine (257 mg, 0.89 mmol) at 0° C. and the mixture was stirred for 2 h allowing the mixture to warm to 20° C. The solvent was removed in vacuo, and the residue was purified by silica column chromatography (20 cm column, ethyl acetate/hexane, 1/1-3/1; methylene chloride/methanol 30/1-15/1) to afford 267 mg (92%) of 5-[3-[4-(2-methyl-tetrazol-5-yl)phenoxy]propyl]-1-methyl-2-ethylimidazole, as a white crystalline solid, m.p. 115°–117° C. (recrystallization from methylene chloride/hexane).

G. Compounds of the formula I wherein R$_1$ and R$_2$ are the same and are in the 3,5 positions of the phenoxy ring, R$_3$ is 2-methyl tetrazolyl and Y is 1,3-propylene and AZO is X-(R$_4$, 1-methyl-imidazolyl)

The following were prepared using the methods described above.

| Example | R$_1$ = R$_2$ | R$_4$ | X | M.P. |
|---|---|---|---|---|
| G1 | CH$_3$ | H | 5 | 100–102 |
| G2 | CH$_3$ | 2 ethyl | 4 | 55–57 |
| G3 | H | 2 ethyl | 4 | 99–101 |
| G4 | CH$_3$ | H | 4 | 82–84 |
| G5 | H | H | 4 | 122–124 |

EXAMPLE 11

A. 3-Methyl-5-[3-[4-(2-methyl-tetrazol-5-yl)-2,6-dimethylphenoxy]-propyl]-thiazole (I, Azo=3-methylthiazol-5-yl, Y=1,3-propylene, R$_1$,R$_2$=3,5-dimethyl, R$_3$=2-methyl-tetrazol-5-yl)

n-BuLi (2.5M, 1.33 ml, 3.33 mmol) was added slowly at −78° C. to a solution of 3-methyl-thiazole (300 mg, 3.03 mmol) in 8 ml of THF under nitrogen. After stirring at −78° C. for 15 min, HMPA (1.08 g, 6.06 mmol) was added and the resulting mixture was stirred for 10 min. To the above mixture was added at −78° C. 3-[4-(2-methyl-tetrazol-5-yl)-2,6-dimethylphenoxy]-propylbromide (985 mg, 3.03 mmol) in 5 ml of THF. The mixture was allowed to warm to 20° C. and stirred for 3 h. Saturated ammonium chloride solution was added and the aqueous layer was extracted with ether (3×), and the organic layer was dried over sulfate and concentrated in vacuo. The residue was purified by silica column chromatography (15 cm column, ethyl acetate/hexane, 1/8-3/1) to afford 290 mg (28%) of 3-methyl-5-[3-[4-(2-methyl-tetrazol-5-yl)-2,6-dimethylphenoxy]-propyl]thiazole.

EXAMPLE 12

A. 2-[4-(4-Cyano-2, 6-dimethylphenoxy)butyl]-dioxalane

To a mixture of 4-cyano-2,6-dimethylphenol (10.37 g, 70.6 mmol), 150 ml of NMP, potassium carbonate (10.2 g, 74 mmol), and 3.3 g (20 mmol) of potassium iodide was added 2-(3-chlorobutyl)-1,3-dioxalane (11.06 g, 67.2 mmol) slowly, and the mixture was stirred at 75° C. overnight. After cooling, the mixture was poured into 1000 ml of water and extracted with ether (4×750 ml). The combined organic layer was washed with 10% NaOH solution (3×100 ml), brine (170 ml), and dried over sodium sulfate and filtered. The organic filtrate was concentrated in vacuo, and the residue was purified by silica column chromatography (10 cm column, ethyl acetate/hexane, 1/5-1/1 ) to afford 17.8 g (96%) of 2-[4-(4-cyano-2,6-dimethylphenoxy)butyl]-dioxalane, as a white solid, m.p. 61°–62° C. (recrystallization from methylene chloride/hexane).

B. 5-(4-Cyano-2,6-dimethylphenoxy)pentyraldehyde

A mixture of 2-[4-(4-cyano-2, 6-dimethylphenoxy)butyl] dioxalane (4.6 g, 16.7 mmol), 54 ml of acetic acid and 8 ml of water was stirred at 90° C. for 24 h. The solution was diluted with ice and basified with 35% NaOH, 2N NaOH solution, and saturated sodium bicarbonate solution (pH=7). The aqueous layer was extracted with ether (3×), the combined organic layer was dried over sodium sulfaste and concentrated. The residue was purified by silica column chromatography (20 cm column, methylene chloride/ acetone, 1/0-100/1) to afford 3.1 g (80%) of 5-(4-cyano-2, 6-dimethylphenoxy)pentyraldehyde, as a white solid (recrystallization from ethyl acetate/hexane)

C. 5-(4-Cyano-2,6-dimethylphenoxy)-2-bromopentyraldehyde

A mixture of 5-(4-cyano-2,6-dimethylphenoxy) pentyraldehyde (1.7 g, 3.68 mmol) and 5,5-dibromobarbituric acid (1.05 g, 3.68 mmol) in 90 ml of THF was stirred at 75° C. for 26 h. The solvent was removed in vacuo, the residue was redissolved in methylene chloride, filtered through a short silica column (8 cm, methylene chloride), and concentrated in vacuo to afford 2.15 g (94%) of 5-(4-cyano-2,6-dimethylphenoxy)-2-bromopentyraldehyde, as a viscous oil. A sample was further purified by silica column chromatography (20 cm, methylene chloride/hexane, 1/1-1/10) followed by recrystallization from ethyl acetate/hexane to afford a white solid, m.p. 47°–49° C.

D. 5-[3-(4-Cyano-2,6-dimethylphenoxy)propyl]-2-methylthiazole

A mixture of 5-(4-cyano-2,6-dimethylphenoxy)-2-bromopentyraldehyde (1.8 g, 6.4 mmol) and thioaceamide (0.48 g, 6.4 mmol) in 50 ml of dichloroethane was stirred at 85° C. for 18 h. The solvent was removed in vacuo, an aqueous sodium bicarbonate solution was added to the residue, and the aqueous layer was extracted with methylene chloride. The organic layer was dried over sodim sulfate, concentrated in vacuo, and the residue was purified by silica column chromatography (20 cm column, ethyl acetate/ hexane 1/5-1/1) to afford 1.2 g (72%) of 5-[3-(4-cyano-2, 6-dimethylphenoxy)propyl]-2-methylthiazole, as an oil which was crystallized from ethyl acetate/hexane to yield a yellow-white solid, m.p. 64°–66° C.

E. 5-[3-(4-Aminohydroximinomethyl-2,6-dimethylphenoxy)propyl]-2-methylthiazole

Potassium carbonate (2.43 g, 17.58 mmol) was added to a stirred solution of 815 mg (11.72 mmol) of hydroxylamine hydrochloride in 12 ml of absolute ethanol. The mixture was stirred at 80° C. for 15 min, then at 20° C. for 45 min. To the above mixture was added 5-[3-(4-cyano-2,6-dimethylphenoxy)propyl]-2-methylthiazole (837 mg, 2.93 mmol) and the mixture was stirred at 80° C. for 16 h. The mixture was filtered, the residue was washed with hot ethanol, and the filtrate was concentrated in vacuo to yield 1.24 g of 5-[3-(4-aminohydroximino-methyl-2,6-dimethylphenoxy)propyl]-2-methylthiazole as a white solid.

F. 5-[3-[4-(5-Methyl-1,2,4-oxadiazol-3-yl)-2,6-dimethylphenoxy]-propyl]-2-methylthiazole(Azo=2-methyl-5-thiazolyl, Y=1,3-propylene, $R_1,R_2$=3,5-dimethyl, $R_3$=5-methyl-1,2,4-oxadiazol-3-yl)

To a warm (45° C.) solution of 5-[3-(4-aminohydroxyiminomethyl-2,6-dimethylphenoxy)propyl]-2-methylthiazole (308 mg, 0.8 mmol)) in 5 ml of pyridine was added 126 mg (1.6 mmol) of acetyl chloride dropwise, and the resulting mixture was stirred at 110° C. for 16 h, cooled, and diluted with water. The mixture was extracted with ether (4×), and the organic layer was washed with water and dried over sodium sulfate. The organic layer was concentrated in vacuo and a residue was purified by silica column chromatography (20 cm, ethyl acetate/hexane, 1/5-4/1) to afford 182 mg (66%) of 5-[3-[4-(5-methyl-1,2,4-oxadiazol-3-yl)-2,6-dimethylphenoxy]-propyl]-2-methylthiazole, as white crystalline solids, m.p. 60°–62° C.

G. 5-[3-[4-(5-Trifluoromethyl-1,2,4-oxadiazol-3-yl)-2,6-dimethylphenoxy]-propyl]-2-methylthiazole(Azo=2-methyl-5-thiazolyl, Y=1,3-propylene, $R_1,R_2$=3,5-dimethyl, $R_3$=5-trifluoromethyl-1,2,4-oxadiazol-3-yl)

To a solution of 5-[3-(4-aminohydroxyimino-methyl-2,6-dimethylphenoxy)propyl]-2-methylthiazole (593 mg, 1.54 mmol)) in 10 ml of pyridine was added at 20° C. 645 mg (3.07 mmol) of trifluoroacetic anhydride dropwise, and the resulting mixture was stirred at 110° C. for 40 h. The solvent was removed in vacuo, the residue cooled, and diluted with water. The mixture was extracted with ether (3×), and the organic layer was dried over sodium sulfate. The organic layer was concentrated in vacuo and a residue was purified by silica column chromatography (20 cm, ethyl acetate/ hexane, 1/10-1/3) to afford 256 mg (42%) of 5-[3-[4-(5-trifluoromethyl-1,2,4-oxadiazol-3-yl)-2,6-dimethylphenoxy]-propyl]-2-methylthiazole, as white crystalline solids, m.p. 62°–64° C. (recrystallization from ethyl acetate/hexane).

H. 5-[3-[4-(5-Difluoromethyl-1,2,4-oxadiazol-3-yl)-2,6-dimethylphenoxy]-propyl]-2-methylthiazole(Azo=2-methyl-5-thiazolyl, Y=1,3-propylene, $R_1,R_2$=3,5-dimethyl, $R_3$=5-difluoromethyl-1,2,4-oxadiazol-3-yl)

A mixture of 5-[3-(4-aminohydroxyimino-methyl-2,6-dimethylphenoxy)propyl]-2-methylthiazole (1.12 g, 3.5 mmol)) in 14 ml of NMP and 7 ml of ethyl difluoroacetate was stirred at 105° C. for 16 h. The mixture was cooled, partially concentrated in vacuo, and diluted with water. The mixture was extracted with ether (3×), and the organic layer was dried over sodium sulfate. The organic layer was concentrated in vacuo and a residue was purified by silica column chromatography (20 cm, ethyl acetate/hexane, 1/10-1/1) to afford 520 mg (39%) of 5-[3-[4-(5-difluoromethyl-1,2,4-oxadiazol-3-yl)-2,6-dimethylphenoxy]-propyl]-2-methylthiazole, as white needles (from methylene chloride/ hexane).

EXAMPLE 13

A. 5-[3-(4-Cyano-2,6-dimethylphenoxy)propyl]-2-ethylthiazole

A mixture of 5-(4-cyano-2,6-dimethylphenoxy]-2-bromopentyraldehyde (310 mg, 1 mmol) and thiopropionamide (98 mg, 1.1 mmol) in 8 ml of dichloroethane was stirred at 85° C. for 16 h. The solvent was removed in vacuo, an aqueous sodium bicarbonate solution was added to the residue, and the aqueous layer was extracted with methylene chloride (3x). The organic layer was dried over sodium sulfate, concentrated in vacuo, and the residue was purified by silica column chromatography (20 cm column, ethyl acetate/hexane 1/5-1/1) to afford 246 mg (82%) of 5-[3-(4-cyano-2,6-dimethylphenoxy)propyl]-2-ethylthiazole, m.p. 52°–53° C.

B. 5-[3-(4-Aminohydroximinomethyl-2,6-dimethylphenoxy)propyl]-2-ethylthiazole

Potassium carbonate (4.97 g, 36 mmol) was added to a stirred solution of 1.67 g (24 mmol) of hydroxylamine hydrochloride in 24 ml of absolute ethanol. The mixture was stirred at 80° C. for 15 min, then at 20° C. for 45 min. To the above mixture was added 5-[3-(4-cyano-2,6-dimethylphenoxy)propyl]-2-ethylthiazole (1.8 g, 6 mmol) and the mixture was stirred at 80° C. for 18 h. The hot mixture was filtered, the residue was washed with hot ethanol, and the filtrate was concentrated in vacuo to yield 2.18 g of 5-[3-(4-aminohydroxyimino-methyl-2,6-dimethylphenoxy)propyl]-2-ethylthiazole as a white solid.

C. 5-[3-[4-(S-Trifluoromethyl-1,2,4-oxadiazol-3-yl)-2,6-dimethylphenoxy]-propyl]-2-ethylthiazole(Azo=2-ethyl-5-thiazolyl, Y=1,3-propylene, $R_1,R_2$=3,5-dimethyl, $R_3$=5-trifluoromethyl-1,2,4-oxadiazol-3-yl)

To a solution of 5-[3-(4-aminohydroximino-methyl-2,6-dimethylphenoxy)propyl]-2-methylthiazole (800 mg, 2.4 mmol)) in 16 ml of pyridine was added at 20° C. 1.008 g (4.8 mmol) of trifluoroacetic anhydride dropwise, and the resulting mixture was stirred at 20° C. for 5 h, and then at 110° C. for 40 h. The solvent was removed in vacuo, the residue cooled, and diluted with water. The mixture was extracted with ether (3x), and the organic layer was dried over sodium sulfate. The organic layer was concentrated in vacuo and a residue was purified by silica column chromatography (20 cm, ethyl acetate/hexane, 1/10-1/3) to afford 333 mg (34%) of 5-[3-[4-(5-trifluoromethyl-1,2,4-oxadiazol-3-yl)-2,6-dimethylphenoxy]-propyl]-2-ethylthiazole, as white crystalline solids, m.p. 57°–59° C. (recrystallization from ethyl acetate/hexane).

D. 5-[3-[4-(5-Methyl-1,2,4-oxadiazol-3-yl)-2,6-dimethylphenoxy]-propyl]-2-ethylthiazole(Azo=2-ethyl-5-thiazolyl, Y=1,3-propylene, $R_1,R_2$=3,5-dimethyl, $R_3$=5-methyl-1,2,4-oxadiazol-3-yl)

To a solution of 5-[3-(4-aminohydroximino-methyl-2,6-dimethylphenoxy)propyl]-2-methylthiazole (308 mg, 0.8 mmol)) in 6 ml of pyridine was added 200 mg (0.6 mmol) of acetyl chloride dropwise at 20° C., and the resulting mixture was stirred at 110° C. for 18 h, cooled, and diluted with water. The mixture was extracted with ether (3x), the organic layer was washed with water and dried over sodium sulfate. The organic layer was concentrated in vacuo and a residue was purified by silica column chromatography (20 cm, ethyl acetate/hexane, 1/5-2/1) to afford 135 mg (63%) of 5-[3-[4-(5-methyl-1,2,4-oxadiazol-3-yl)-2,6-dimethylphenoxy]-propyl]-2-ethylthiazole, as white crystalline solids, m.p. 43°–45° C.

E. 5-[3-[4-(5-Difluoromethyl-1,2,4-oxadiazol-3-yl)-2,6-dimethylphenoxy]-propyl]-2-ethylthiazole(Azo=2-ethyl-5-thiazolyl, Y=1,3-propylene, $R_1,R_2$=3,5-dimethyl, $R_3$=5-difluoromethyl-1,2,4-oxadiazol-3-yl)

A mixture of 5-[3-(4-aminohydroximino-methyl-2,6-dimethylphenoxy)propyl]-2-ethylthiazole (600 mg, 1.8 mmol)) in 7.2 ml of NPM and 3.6 ml of ethyl difluoroacetate was stirred at 105° C. for 19 h. The mixture was cooled, partially concentrated in vacuo, and diluted with water. The mixture was extracted with ether (3x), and the organic layer was dried over sodium sulfate. The organic layer was concentrated in vacuo and a residue was purified by silica column chromatography (20 cm, ethyl acetate/hexane, 1/10-1/1) to afford 297 mg (42%) of 5-[3-[4-(5-difluoromethyl-1,2,4-oxadiazol-3-yl)-2,6-dimethylphenoxy]-propyl]-2-ethylthiazole, as a white solid, m.p. 68°–70° C.

F. 5-[3-(4-Cyano-2,6-dimethylphenoxy)propyl]-thiazole

To a mixture of phosphorus pentasulfide (760 mg, 1.71 mmol) and 8 ml of dioxane was added rapidly dropwise formamide (570 mg, 12.67 mmol), and the mixture was stirred at 65° C. for 10 min and cooled. To the above mixture was added in portions 5-(4-cyano-2,6-dimethylphenoxy)-2-bromopentyraldehyde (2.62 g, 8.45 mmol), and the mixture was stirred at 65° C. for 20 min and then refluxed for 60 min. After adding 5 ml of water and 1 ml of conc. HCl the mixture was refluxed another hour. The above mixture was basified with 2N NaOH solution and sodium bicarbonate solution (to pH=8). The aqueous layer was extracted with methylene chloride, the organic layer was dried over sodium sulfate, and concentrated in vacuo. The residue was purified by silica column chromatography (20 cm column, ethyl acetate/hexane 1/5-1/1) to afford 1.11 g (48%) of 5-[3-(4-cyano-2,6-dimethylphenoxy)propyl]-thiazole, as an oil which was crystallized from ethyl acetate/hexane to yield a white solid, m.p. 71°–73° C.

G. 5-[3-(4-Aminohydroximinomethyl-2,6-dimethylphenoxy)propyl]-thiazole

Potassium carbonate (3.07 g, 22.3 mmol) was added to a stirred solution of 1.03 g (14.8 mmol) of hydroxylamine hydrochloride in 15 ml of absolute ethanol. The mixture was stirred at 80° C. for 15 min, then at 20° C. for 45 min. To the above mixture was added 5-[3-(4-cyano-2,6-dimethylphenoxy)propyl]-thiazole (1.01 g, 3.71 mmol) and the mixture was stirred at 80° C. for 20 h. The mixture was filtered, the residue was washed with hot ethanol, and the filtrate was concentrated in vacuo to yield 1.26 g of 5-[3-(4-aminohydroximino-methyl-2,6-dimethylphenoxy)propyl]thiazole as a white solid.

H. 5-[3-[4-(5-Trifluoromethyl-1,2,4-oxadiazol-3-yl)-2,6-dimethylphenoxy]-propyl]-thiazole(Azo=5-thiazolyl, Y=1,3-propylene, $R_1,R_2$=3,5-dimethyl, $R_3$=5-trifluoromethyl-1,2,4-oxadiazol-3-yl)

To a solution of 5-[3-(4-aminohydroximino-methyl-2,6-dimethylphenoxy)propyl]-thiazole (450 mg, 1.48 mmol)) in 15 ml of pyridine was added 620 mg (2.95 mmol) of trifluoroacetic anhydride dropwise. The resulting mixture was stirred at 20° C. for 2 h, and then at 110° C. for 18 h. The solvent was removed in vacuo, the residue diluted with water, and the mixture was extracted with ether (3x). The organic layer was dried over sodium sulfate, concentrated in vacuo and a residue was purified by silica column chromatography (20 cm, ethyl acetate/hexane, 1/8-1/2) to afford 190 mg (34%) of 5-[3-[4-(5-trifluoromethyl-1,2,4-oxadiazol-3-yl)-2 6-dimethylphenoxy]-propyl]-thiazole, as white crystalline solids, m.p. 95°–97° C.

I. 5-[3-[4-(5-Difluoromethyl-1,2,4-oxadiazol-3-yl)-2,6-dimethylphenoxy]-propyl]-thiazole(Azo=5-thiazolyl, Y=1,3-propylene, $R_1,R_2$=3,5-dimethyl, $R_3$=5-difluoromethyl-1,2,4-oxadiazol-3-yl)

A mixture of 5-[3-(4-aminohydroximino-methyl-2,6-dimethylphenoxy)propyl]-thiazole (506 mg, 1.66 mmol), 5 ml of NMP and 3.3 ml fo ethyl difluoroacetate was stirred at 105° C. for 20 h. The solvent was partially removed in vacuo, the residue was cooled and diluted with water. The mixture was extracted with ether (3x), and the organic layer was dried over sodium sulfate. The organic layer was concentrated in vacuo and a residue was purified by silica column chromatography (20 cm, ethyl acetate/hexane, 1/5-1/2) to afford 212 mg (35%) of 5-[3-[4-(5-difluoromethyl-1,2,4-oxadiazol-3-yl)-2,6-dimethylphenoxy]-propyl]thiazole, as white crystalline solids, m.p. 78°–80° C. (recrystallization from ethyl acetate/hexane).

EXAMPLE 14

A. 2-[4-[4-(2-Methyl-tetrazol-5-yl)-2, 6-dimethylphenoxy]butyl]-dioxalane

To a mixture of 4-(2-methyl-tetrazol-5-yl)-2,6-dimethylphenol (7.54 g, 37 mmol), 75 ml of NMP, potassium carbonate (5.1 g, 37 mmol), and 1.67 g (10 mmol) of potassium iodide was added 2-(4-chlorobutyl)-1,3-dioxalane (5.53 g, 33.6 mmol) dropwise, and the mixture was stirred at 80° C. overnight. After cooling, the mixture was poured into 500 ml of water, and extracted with ether (4×125 ml). The combined organic layer was washed with 10% NaOH solution(5×100 ml), brine (80 ml), and dried over sodium sulfate and filtered. The organic filtrate was concentrated in vacuo, and the residue was purified by recrystallization from methylene chloride/hexane to afford 6.78 g (61%) of 2-[4-[4-(2-methyl-tetrazol-5-yl)-2,6-dimethylphenoxy]-butyl]-dioxalane. The product was further purified by silica column chromatography (12 cm, ethyl acetate/hexane, 1/5-1/2) followed by recrystallization from methylene chloride/hexane, m.p. 57°–59° C.

B. 5-[4-(2-Methyl-tetrazol-5-yl)-2,6-dimethylphenoxy]pentylaldehyde

2-[4-[4-(2-Methyl-tetrazol-5-yl)-2, 6-dimethylphenoxy]butyl]-dioxalane (4.3 g, 12.95 mmol) was dissolved in 42 ml of acetic acid and 5 ml of water and the mixture was stirred at 90° C. for 24 h. The solution with ice was basified with 35% NaOH solution, 2N NaOH solution, and sodium bicarbonate solution (to pH=7). The above mixture was extracted with ether (3×), and the combined organic layer was dried over sodium sulfate and concentrated. The residue was purified by silica column chromatography (methylene chloride/acetone, 1/0-50/1) followed by recrystallization from methylene chloride/hexane to afford 2.4 g (64%) of 5-[4-(2-methyl-tetrazol-5-yl)-2,6-dimethylphenoxyl]-pentylaldehyde, m.p. 50°–52° C.

C. 5-[4-(2-Methyl-tetrazol-5-yl)-2,6-dimethylphenoxy]-2-bromopentyl-aldehyde

A mixture of 5-[4-(2-methyl-tetrazol-5-yl)-2,6-dimethylphenoxy]pentylaldehyde (1.94 g, 9.74 mmol) and 5,5-dibromobarbituric acid (0.96 g, 3.37 mmol) in 80 ml of ether was stirred at 20° C. for 20 h. The mixture was filtered and the residue was washed with ether (2×). The combined organic layer was dried over sodium sulfate, concentrated in vacuo, and the residue was purified by silica column chromatography (12 cm, methylene chloride/acetone, 1/0-50/1) followed by recrystallization from methylene chloride/hexane to afford 1.69 g (68%) of 5-[4-(2-methyl-tetrazol-5-yl)-2,6-dimethylphenoxyl-2-bromopentyl-aldehyde, as a white solid, m.p. 62°–64° C.

D. 5-[3-[4-(2-Methyl-tetrazol-5-yl)-2,6-dimethylphenoxy]propyl]-2-methylthiazole (I, Azo=2-methyl-5-thiazolyl, Y=1,3-propylene, $R_1,R_2$=3,5-dimethyl, $R_3$=2-methyltetrazol-5-yl)

A mixture of 5-[4-(2-methyl-tetrazol-5-yl)-2,6-dimethylphenoxy]-2-bromo-pentylaldehyde (367 mg, 1 mmol) and thioaceamide (68 mg, 0.9 mmol) in 10 ml of dichloroethane was stirred at 85° C. for 22 h. The solvent was removed in vacuo, an aqueous sodium bicarbonate solution was added to the residue, the aqueous layer was extracted with methylene chloride. The organic layer was dried over sodium sulfate, concentrated in vacuo, and the residue was purified by silica column chromatography (20 cm column, ethyl acetate/hexane 1/5-4/1) followed by recrystallization from methylene chloride/hexane to afford 214 mg (70%) of 5-[3-[4-(2-methyl-tetrazol-5-yl)-2,6-dimethylphenoxy]-propyl]-2-methylthiazole, as an oil which was crystallized from ethyl acetate/hexane to yield a yellow-white solid, m.p. 86°–88° C.

EXAMPLE 15

A compound of formula I wherein (AZO) is triazine was prepared by the following route:

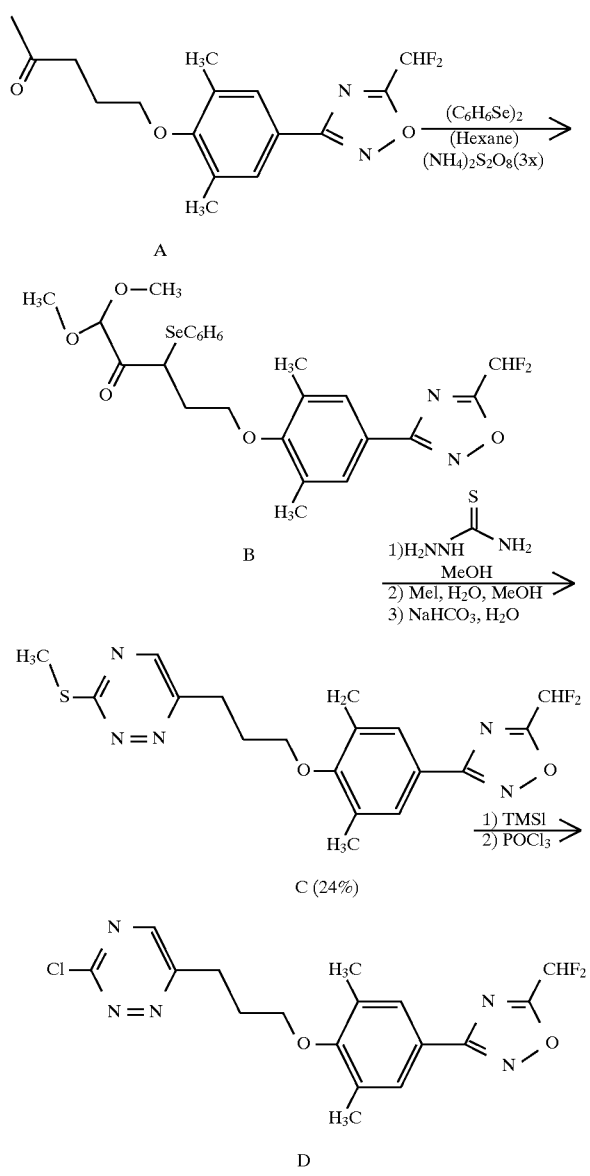

E. By replacing $H_2NNH\ CSNH_2$ in the formation of example 19C, with $H_2NNC(CH_3)$-$NH_2$ one obtains an intermediate which, upon heating in triethylamine, forms a compound of formula I, m.p. 86°–88° C. (23%) (AZO=5-(3-methyl)1,2,4-triazinyl, Y=1,3-propyl, $R_1,R_2$=3,5-dimethyl, $R_3$=5-difluoromethyl 1,2,4-oxadiazol-3-yl.

F. Using the method of 19E but substituting the appropriate hydrazinyl reactant one obtains compounds of formula I wherein Y=1,3-propylene, $R_1,R_2$=3,5-dimethyl, $R_3$=5-difluoromethyl-1,2,4-oxadiazolyl, AZO=5-(3-ethyl)-1,2,4-triazinyl m.p. 85°–87° C. (23% yield).

G. Using the method of example 11E but replacing the staring material of 11A with 4-(3-acetyl-propyloxy)-3,5-dimethyl benzonitrile one obtains an intermediate which, when reacted with hydroxyl amine and then trifluoroacetic an hydride in pyridine (as described above) one obtains a compound of formula I wherein AZO=5-(3-methyl)-1,2,4-triazinyl; Y=1,3-propylene, $R_1,R_2$=3,5-dimethyl, $R_3$=5-trifluoromethyl-1,2,4-oxadiazol-3-yl); (50% yield).

EXAMPLE 16

5-[4-(5-Methyl-1,2,4-oxadiazol-3-yl)propyloxy-3,5-dimethyl]phenyl-2-methyl-tetrazole(AZO-Y-=5-methyl-1,2,4-oxadiazol-3-yl)propyl, $R_1,R_2$=3,5-dimethyl, $R_3$=2-methyltetrazol-5-yl)

A solution of sodium methoxide (prepared under argon from 56 mg (1.2 eq) of sodium and 2 ml of methanol) was added to a stirred solution of 166 mg (1.2 eq) of hydroxylamine hydrochloride in 2 ml of methanol under argon. The mixture was stirred for 1 h at room temperature, 540 mg (20 mmol) of 5-[4-(3-cyano)propyloxy-3,5-dimethyl]phenyl-2-methyltetrazole was added and the resulting mixture was allowed to reflux for 26 h. After adding an additional mixture of sodium methoxide (180 mg of Na in 5 ml of methanol) and hydroxylamine hydrochloride (520 mg; 7.8 mmol), the resulting reaction mixture was allowed to reflux overnight. The mixture was filtered, the filtrate concentrated in vacuo, and the residue (800 mg) was purified by a flash column chromatography (75 mg of silica gel; 25% of methanol in methylene chloride) to afford 270 mg (44%) of 5-[4-(3-aminohydroxyiminomethyl)-propyloxy-3,5-dimethyl]phenyl-2-methyl-tetrazole.

To a solution of 440 mg (1.45 mmol) of 5-[4-(3-aminohydroxyiminomethyl)-propyloxy-3, 5-dimethyl]phenyl-2-methyl-tetrazole in 3 ml of pyridine (with stirring and slight warming) was added rapidly dropwise 0.21 ml (2.84 mmol) of acetyl chloride and the resulting mixture was gently refluxed for 2 h. The reaction mixture was cooled, diluted with water, chilled on ice bath, and the solids were filtered and washed with excess water (150 ml) to remove pyridine. The solid product was dissolved in methylene chloride, dried over magnesium sulfate, filtered through a florisil pad, and the organic layer was concentrated in vacuo to yield 270 mg of a tan solid. The tan solid product was purified through MPLC column (120 g Keiselgel, 50% ethyl acetate/hexane, 25 ml fractions, 25 ml/min), and recrystallization from methanol to afford 210 mg (44.7%) of 5-[4-(5-methyl-1,2,4-oxadiazol-3-yl)propyloxy-3,5-dimethyl]phenyl-2-methyl-tetrazole as clear crystalline solid, m.p. 105.5°–106.5° C.

EXAMPLE 17

A. 3-[4-(2-Methyl-tetrazol-5-yl)-2,6-dimethylphenoxy] propylbromide

A mixture of (3-hydroxypropyl)-bromide (2.17 ml, 24 mmol), 4-(2-methyl-tetrazol-5-yl)-2,6-dimethylphenol (5.1 g, 25 mmol), and DEAD (4.18 g, 24 mmol) was dissolved in 50 ml of THF at 0° C. To the above solution was added dropwise triphenylphosphine (6.3 g, 24 mmol) at 0° C. and the mixture was allowed to stir at 0° C. for 0.5 h. The mixture was diluted with 500 ml of water and 100 ml of ether, and the aqueous layere was extracted with ether (2×400 ml). The combined organic layer was dried over sodium sulfate, and concentrated in vacuo. The residue was dissolved in 800 ml of ether, and the organic layer was washed with 10% NaOH solution (3×50 ml), dried over sodium sulfate, and concentrated in vacuo. The residue was purified by silica column chromatography (7 cm column, ethyl acetate/hexane, 1/5) followed by recrystallization from methylene chloride/hexane to afford 6.4 g (82%) of 3-[4-(2-methyl-tetrazol-5-yl)-2,6-dimethylphenoxyl]-propylbromide, as a light yellow oil.

B. 5-Carbomethoxy-2-[3-[4-(2-methyl-tetrazol-5-yl)-2,6-dimethylphenoxy]-propyl]-1,2,4-triazole (I, Azo=5-carbomethoxy-1,2,4-triazol-2-yl, Y=1,3-propylene, $R_1,R_2$=3,5-dimethyl, $R_3$=2-methyl-tetrazol-5-yl)

Hexane washed 60% NaH (22 mg, 0.55 mmol) in 0.5 ml of DMF was added at 20° C. to a solution of 5-carbomethoxy-1,2,4-triazole (63.5 mg, 0.5 mmol) in 0.5 ml of DMF and the mixture was stirred for 1 h. To the above mixture was added at 20° C. 3-[4-(2-methyl-tetrazol-5-yl)-2,6-dimethylphenoxy]-propylbromide (163 mg, 0.5 mmol) in 0.5 ml of DMF and the mixture was stirred at 20° C. for 18 h. The mixture was partitioned between ice/water and ethyl acetate. The aqueous layer was extracted with ethyl acetate (3×), and the organic layer was dried over sodium sulfate and concentrated in vacuo. The residue was purified by silica column chromatography (20 cm column, ethyl acetate/hexane, 1/5-1/0; methylene chloride/acetone) to afford 74 mg (40%) of 5-carbomethoxy-2-[3-[4-(2-methyl-tetrazol-5-yl)-2,6-dimethylphenoxy]-propyl]-1,2,4-triazole.

C. 5-Hydroxymethyl-2-[3-[4-(2-methyl-tetrazol-5-yl)-2,6-dimethylphenoxy]-propyl]-1,2,4-triazole (I, Azo=5-hydroxymethyl-1,2,4-triazol-2-yl, Y=1,3-propylene, $R_1,R_2$=3,5-dimethyl, $R_3$=2-methyl-tetrazol-5-yl)

To a solution of 5-carbomethoxy-2-[3-[4-(2-methyl-tetrazol-5-yl)-2,6-dimethylphenoxy]-propyl]-1,2,4-triazole (37.1 mg, 0.1 mmol) in 1 ml of THF was added at 0° C. a solution of 1M LAH in THF (65 ul, 1M in THF, 0.065 mmol). The mixture was stirred for 10 min at 0° C. and then stirred at 20° C. for 24 h. Rochelle salt solution was added to the mixture and the solution was stirred at 20° C. for 10 min. Ethyl acetate was added to the above mixture, the aqueous layer was extracted with methylene chloride (3×), and the combined organic layer was dried over sodium sulfate and concentrated in vacuo. The residue was purified by silica column chromatography (10 cm column, ethyl acetate/hexane, 1/1-1/0; methylene chloride/acetone, 2/1-1/2) to afford 27 mg (79%) of 5-hydroxymethyl-2-[3-[4-(2-methyl-tetrazol-5-yl)-2,6-dimethylphenoxy]-propyl]-1,2,4-triazole, as a white solid.

D. 5-Phenoxythiocarbonyloxymethyl-2-[3-[4-(2-methyltetrazol-5-yl)-2, 6-dimethylphenoxy]-propyl]-1,2,4-triazole To a mixture of 5-hydroxymethyl-2-[3-[4-(2-methyl-tetrazol-5-yl)-2,6-dimethyl-phenoxy]-propyl]-1,2,4-triazole (343 mg, 1 mmol) in 15 ml of acetonitrile was added DMAP (244 mg, 2 mmol) and phenyl chlorothioformate (381 mg, 2.2 mmol). The mixture was stirred at 20° C. for 7 h, an additional phenyl chlorothioformate (1 equiv) was added, and the mixture was stirred for 15 h. The solvent was removed in vacuo and 5-phenoxythiocarbonyloxymethyl-2-[3-[4-(2-methyl-tetrazol-5-yl)-2,6-dimethylphenoxy]-propyl]-1,2,4-triazole was isolated and used without further purification.

E. 5-Methyl-2-[3-[4-(2-methyl-tetrazol-5-yl)-2,6-dimethylphenoxy]-propyl]-1,2,4-triazole (I, Azo=5-methyl-1,2,4-triazol-2-yl, Y=1,3-propylene, $R_1,R_2$=3,5-dimethyl, $R_3$=2-methyl-tetrazol-5-yl)

To a solution of 5-phenoxythiocarbonyloxymethyl-2-[3-[4-(2-methyl-tetrazol-5-yl)-2,6-dimethylphenoxy]-propyl]-1,2,4-triazole (130 mg, 0.79 mmol) in 20 ml of toluene was added AIBN (130 mg, 0.79 mmol) and tributyltin hydride (3.2 g, 11 mmol) and the mixture was stirred at 75° C. for 6.5 h. The solvent was concentrated in vacuo and the residue was purified by silica column chromatography (10 cm column, ethyl acetate/hexane, 1/1-5/1; methylene chloride/acetone, 4/1-0/1) to afford 142 mg (43%) of 5-methyl-2-[3-[4-(2-methyl-tetrazol-5-yl)-2,6-dimethylphenoxy]-propyl]-1,2,4-triazole, m.p. 101°–103° C.

F. 2-[3-[4-(2-Methyl-tetrazol-5-yl)-2, 6-dimethylphenoxy] propyl]-1,2,4-triazole (I, Azo=1,2,4-triazol-2-yl, Y=1,3-propylene, $R_1, R_2$=3,5-dimethyl, $R_3$=2-methyltetrazol-5-yl)

To a solution of 5-carbomethoxy-1-[3-[4-(2-methyl-tetrazol-5-yl)-2,6-dimethylphenoxy]-propyl]-1,2,4-triazole (868 mg, 2.34 mmol) in 23 ml of THF was added dropwise at 0° C. a solution of 1M LAH in THF (1.52 ml, 1.52 mmol). The mixture was stirred for 20 min at 0° C. and then stirred at 20° C. for 24 h. Rochelle salt solution was added to the mixture and the solution was stirred at 20° C. for 10 min. Ethyl acetate was added to the above mixture and the aqueous layer was extracted with methylene chloride (3×). The combined organic layer was dried over sodium sulfate and concentrated in vacuo. The residue was purified by silica column chromatography (16 cm column, methylene chloride/acetone, 8/1-0/1) to afford 132 mg (18%) of 2 -[3-[4-(2-methyl-tetrazol-5-yl)-2,6-dimethylphenoxy] propyl]-1,2,4-triazole, m.p. 76°–78° C.

G. 5-Phenoxythiocarbonyloxymethyl-1-[3-[4-(2-methyletrazol-5-yl)-2,6dimethylphenoxy]-propyl]-1,2,4-triazole To a mixture of 5-hydroxymethyl-1-[3-[4-(2-methyl-tetrazol-5-yl)-2,6-dimethyl-phenoxy]-propyl]-1,2,4-triazole (343 mg, 1 mmol) in 15 ml of acetonitrile was added DMAP (244 mg, 2 mmol) and phenyl chlorothioformate (381 mg, 2.2 mmol). The mixture was stirred at 20° C. for 7 h. An additional phenyl chlorothioformate (1 equiv) was added, and the mixture was stirred for 15 h. The solvent was removed in vacuo and 5-phenoxythiocarbonyloxymethyl-1-[3-[4-(2-methyl-tetrazol-5-yl)-2,6-dimethylphenoxy]-propyl]-1,2,4-triazole was isolated and used without further purification.

H. 5-Methyl-1-[3-[4-(2-methyl-tetrazol-5-yl)-2,6-dimethylphenoxy]3-propyl]-1,2,4-triazole (I, Azo=5-methyl-1,2,4-triazol-1-yl, Y=1,3-propylene, $R_1,R_2$=3,5-dimethyl, $R_3$=2-methyl-tetrazol-5-yl) p To a solution of 5-phenoxythiocarbonyloxymethyl-1-[3-[4-(2-methyl-tetrazol-5-yl)-2,6-dimethylphenoxy]-propyl]-1,2,4-triazole (130 mg, 0.79 mmol) in 20 ml of toluene was added AIBN (130 mg, 0.79 mmol) and tributyltin hydride (3.2 g, 11 mmol) and the mixture was stirred at 75° C. for 6.5 h. The solvent was concentrated in vacuo and the residue was purified by silica column chromatography (13 cm column, ethyl acetate/hexane, 1/1-5/1; methylene chloride/acetone, 4/1-0/1) to afford 61 mg (19%) of 5-methyl-1-[3-[4-(2-methyl-tetrazol-5-yl)-2,6-dimethylphenoxy]-propyl]-1,2,4-triazole, m.p. 126°–128° C.

EXAMPLE 18A 2.38 g of 2-methyl-5-(3,5-dimethyl-4-3[3-methylisoxazol-5-yl]propoxyphenyl)-tetrazol was dissolved in 60 mL of methanol with 2.29 g of ammonium formate and 0.24 g of palladium on carbon and stirred overnight. The mixture was filtered through celite while washing with methanol. The filtrate was concentrated to a grey solid (2.35 g) The solid was extracted with ether and dried over sodium sulfate and was concentrated to a light green solid 1.74 g (73%) of the corresponding β-methyl, β-amino α-unsaturated keto compound which was used without further purification.

The product from preparation above was dissolved in 15 mL of ethanol and 0.3 mL of methylhydrazine was added and the reaction mixture heated to 60° C. overnight. The reaction mixture was concentrated to a pale yellow solid and purified by MPLC (45 to 65% EtOAc/hexane). Two products were obtained, $A_1$, a product according to formula I wherein; azo is 1,5-dimethyl-3-pyrazolyl, Y=1,3-propylene, $R_1$, $R_2$ representes 3,5-dimethyl, $R_3$=2-methyltetrazol-yl, (m.p. 77°–78°, 0.206 g). The other product, $A_2$, was obtained in purified form from recrystallization in ethylacetate in hexane, (m.p. 80°–81C.), 0.115 g was a compound of formula I wherein azo is 1,3-dimethyl-5-pyrazolyl, Y=1,3-propylene, $R_1$, $R_2$ represents 3,5-dimethyl, $R_3$=2-methyl-5-tetrazol-yl.

EXAMPLE 18B-E

Using the method described above compounds of formula I ere prepared where $R_3$ is 2-methyl-5-tetrazolyl; $R_1$, $R_2$ represents 3,5-dimethyl, Y is 1,3-propylene and AZO is 3-($R_4$, $R_5$) pyrazylyl.

| Ex. | $R_4$ | $R_5$ | M.P. |
|---|---|---|---|
| 18b | 5-$CH_3$ | H | 67–69 |
| 18c | 1-$CH_3$ | H | 110–111 |
| 18d | H | H | — |
| 18e | 5-$CH_3$ | 2-$CH_3$ | 80–81 |

EXAMPLE 18F 9 g of [3-(4-bromo-2,6-dimethylphenoxy)propyl] vinylmethylether and 110 mL of triethylorthoformate and 12 mls of boron trifluoride etherate with excess $Na_2CO_3$ was refluxed. Upon cooling the reaction mixture was stirred for 24 hours. After no further gas evolution was observed, the reaction was stirred for 4 additional hours at room temperature. Finally, the reaction mixture was filtered through a glass fritted funnel, the filtrate was concentrated under vacuum yielding 9 g or an oil used in the next step.

To the product obtained above 6.2 g of ethylhydrazine oxalate was added and the mixture refluxed for 24 hours under nitrogen. The reaction mixture was concentrated under vacuum and purified via MPLC to provide the corresponding 1-ethyl-3-(4-bromo-2, 6-dimethylphenoxy) propylpyrazolyl. (yield 32%, 2.2 g).

1.68 g of the product obtained above was combined with 0.446 g of copper/cyanide in DMF and refluxed for 48 hours. The mixture was diluted with 100 mls of an ethyl acetate/water mixture and filtered. The mixture was washed with water, then saturated amoniumchloride and dried over magnesium sulfate, filtered and concentrating yielding 1.2 g of the corresponding cyanide product.

The cyanide obtained above was combined with hydroxylamine hydrochloride and potassium carbonate ethanol and refluxed under nitrogen for 3 days. On work-up as described above, the product was then exposed to difluoroethylacetate resulting in the formation of ta compound of formula I, m.p. 40°–50° C; 114 mgs ($R_1$, $R_2$=3,5-dimethyl, Y=1,3-propylene, azo=1-ethyl-4-pyrazolyl, $R_3$=5-difluoromethyl-1,2,4-oxadiazol-3-yl).

EXAMPLE 18G

Using any of the compounds disclosed in U.S. Pat. No. 5,349,068 it is contemplated that any corresponding compound of formula I can be prepared by the method of Example 18A.

EXAMPLE 19A 1.525 g of 4-(3,5-dimethyl-[2-methyl-5-tetrazolyl] phenoxy)-propionic acid was purified by dissolving the acid in a mixture of 3 mmol sodium hydroxide and washing several times with ethylacetate to remove any impurity. The basic phase was then acidified with concentrated hydrochloric acid to a pH of about 3. A white crystaline solid was filtered and dried to give the purified acid used in the next step.

The acid purified above was dissolved in methylene chloride and 5 mls of thionylchloride was added and the mixture was refluxed for 6 hours. The reaction mixture was then concentrated under vacuum to yield a white solid (m.p. 81°–82° C.). The resulting acid chloride was used in the next step without purification.

Acid chloride from above was dissolved in 50 mL of toluene and 0.34 g of acetichydrazide and 5 drops of triethylamine was added and heated to 90° C. for 8 hours. The resulting reaction mixture was extracted with ethyl acetate, washed with brine, dried over sodium sulfate and concentrated to an off white solid, yielding 1.54 g of the corresponding amide in crude form. This crude product was recrystallized from ether and hexane yielding 0.5 g (32%) of the corresponding amide product.

5 g of 4-hydroxy-3,5-dimethyl-benzonitrile was dissolved in 120 mL of NMP and 5.86 g of $K_2CO_3$ and 0.58 g of KI and 4.8 mL of ethylbromobutyrate was heated to 60° C. for 24 hours. Upon cooling, water was added and an off white precipitate formed. After washing the precipitate with water, 8.90 g (quantitative) of the product was obtained.

The ethyl/ester obtained above was dissolved in 0.82 g of LiOH in an ethanol/water mixture (4:1–120 mls). The reaction mixture was stirred at room temperature, the ethanol was removed by vacuum concentration and the resulting solid product was washed with ether, and then acidified and a white solid was filtered off yielding 6.934 g (88%) of the corresponding acid.

3.9 g of the acid obtained above was dissolved in 120 mls of methylene chloride and 6.0 mls of $SOCl_2$ was heated to reflux for 3 hours. The reaction mixture was allowed to cool and stand over night upon concentration it yielded a yellow oil. To this oil was added a 120 mls of THF and 1.22 g of acetic hydrazide with 5 drops of triethylamine. The reaction mixture was refluxed for three hours, a white percipitate was filtered off and washed with water, dried under high vacuum to yield 3.50 g (72%) of the corresponding 2-methyl-1,3,4-oxadiazol-5-yl compound.

The compound obtained above (azo=2-methyl-1,3,4-oxadiazol-5-yl, Y=1,3-propyl, $R_1$, $R_2$=3,5-dimethyl, $R_3$=CN) was dissolved in 100 mls of ethanol and $NH_2OH\cdot HCl$ and $K_2CO_3$ (2.75 g), the mixture was stirred at room temperature for 46 hours. Off white solids appeared in the flask, these were washed with ethanol, yielding 1.37 g of crude material used in the next step.

This material was dissolved in 15 mL of pyridine and 0.85 mL of trifluoroacetic anhydride was added and the mixture was heated to 80° C. for 3 hours. The reaction mixture was allowed to cool, water was added and the mixture was extracted with methylene chloride and washed with acid and then salt, dried over sodium sulfate and purified by MPLC (50%) ethyl acetate/hexanes. A white solid was obtained and was dried under high vacuum to 0.176 g m.p. 53°–54° C., (Formula I, azo=2-methyl-1,3,4-oxadiazol-5-yl, Y=1,3-propylene, $R_1$, $R_2$=3,5-dimethyl, $R_3$=3-trifluoromethyl-1,2,4-oxadiazol-3-yl).

EXAMPLE 19B

Using the methods described above, a compound of formula I with AZO-Y=3-(5-methyl-1,3,4-oxadiazol-2-yl) propyl and $R_1$, $R_2$=3,5-dimethyl, R3=2-methyl-5-tetrazolyl was prepared, m.p. 74°–76° C.

EXAMPLE 20

As further examples, phenols described only generally thus far can be reacted with any known ω-(Azo)-alkanol, or ω-(Azo)-alkylhalide including any of those described hereinabove using the methods previously described herein to provide a compound of formula I. It is contemplated that any phenol disclosed in allowed application Ser. No. 07/869,287, incorporated herein by reference, is also useful in forming a compound of formula I, using the methods described above. For the reader's convenience the same nomenclature conventions described herein for compounds of formula I are adhered to for phenol intermediates listed below, and a literature reference describing the known phenol is included.

| $R_1$ | $R_2$ | $R_3$ | Reference U.S. Pat. No. |
|---|---|---|---|
| H | H | 1,2,4-oxadiazol-2yl | 4,857,539 |
| H | H | 4,2-dimethyl-2-thiazolyl | 4,857,539 |
| H | H | 2-benzoxazolyl | 4,857,539 |
| 3,5 dichloro | | 3-furanyl | 4,857,539 |
| 3,5 dichloro | | 2-furanyl | 4,857,539 |
| 3,5 dichloro | | 2-thienyl | 4,857,539 |
| 3,5 dichloro | | 2-pyridinyl | 4,857,539 |
| 3,5 dichloro | | 1-methyl-1H-pyrrol-2yl | 4,857,539 |
| 3,5 dichloro | | 3-thienyl | 4,857,539 |
| 3,5 dichloro | | 4-pyridinyl | 4,857,539 |
| 3 nitro | H | benzothiazol-2-yl | 4,857,539 |
| H | H | 2-(4,5-dihydro-4 methyl)oxazolyl | 4,843,087 |
| 3 methyl | H | 2-oxazolyl | 4,843,087 |
| 3 bromo | H | 2-oxazolyl | 4,843,087 |
| 3,5 dimethyl | | 3-methyl-5-isoxazolyl | 4,843,087 |
| 2,6 dimethyl | | 3-methyl-5-isoxazolyl | 4,843,087 |
| H | H | 5-methyl-3-isoxazolyl | 4,942,241 |
| H | H | 4-hydroxy phenyl | (Aldrich) |
| H | H | phenyl | (Aldrich) |
| H | H | 5-ethyl-thiazol-2-yl | 5,100,893 |
| H | H | 4,5-dimethyl-thiazol-2-yl | 5,100,893 |
| H | H | 2-ethyl-thiazol-4-yl | 5,100,893 |
| H | H | 5-ethyl-1,3,4-thiadiazol-2-yl | 5,100,893 |
| H | 3-Cl | 3-ethyl-1,2,4-oxadiazol-5-yl | 5,100,893 |
| H | H | 3-cyclopropyl-1,2,4-oxadiazol-5-yl | 5,100,893 |
| H | H | 3-tbutyl-1,2,4-oxadiazolyl | 5,100,893 |
| H | H | 5-ethyl-1,3,4-oxadiazol-2-yl | 5,100,893 |
| H | H | 3-cyclopropyl,2,4-oxadiazol-5-yl | 5,100,893 |
| H | H | 3-ethyl-1,3,4-thiadiazol-5-yl | 5,100,893 |
| H | | 3-(2hydroxy)propyl-1,2,4-oxadiazol-5-yl | 5,100,893 |
| H | H | 4-ethyl-3-thiazol-2-yl | 5,100,893 |
| H | H | 5-ethyl-3-thiazol-2-yl | 5,100,893 |
| 3-chloro | H | 3-ethyl-1,2,4-oxadiazol-5-yl | 5,100,893 |
| H | H | 4,5-dimethyl-3-thiazol-2-yl | 5,100,893 |
| 2-methoxy | H | 4,5dihydro oxazol-2-yl | 4,843,087 |
| 3-methoxy | H | 4,5dihydro oxazol-2-yl | 4,843,087 |
| 3-chloro | H | 4,5dihydro oxazol-2-yl | 4,843,087 |
| 3-hydroxy | H | 4,5dihydro oxazol-2-yl | 4,843,087 |
| 3,5 di-t-butyl | | 4,5dihydro oxazol-2-yl | 4,843,087 |
| 3-difluoromethyl | H | 4,5dihydro oxazol-2-yl | 4,843,087 |
| 3-hydroxymethyl | H | 4,5dihydro oxazol-2-yl | 4,843,087 |
| 3-carboxy | H | 4,5dihydro oxazol-2-yl | 4,843,087 |
| 2-methyl | 3-hydroxy | 4,5dihydro oxazol-2-yl | 4,843,087 |
| 2,6 dichloro | | 4,5dihydro oxazol-2-yl | 4,843,087 |
| 3,5 difloro | | 4,5dihydro oxazol-2-yl | 4,843,087 |

-continued

| R₁ | R₂ | R₃ | Reference U.S. Pat. No. |
|---|---|---|---|
| 3-chloro | 5-ethynyl | 4,5dihydro oxazol-2-yl | 4,843,087 |

BIOLOGICAL PROPERTIES

Biological evaluation of representative compounds of formula I has shown that they possess antipicornaviral activity. They are useful in inhibiting picornavirus replication in vitro and are primarily active against picornaviruses, including enteroviruses, echovirus and coxsackie virus, especially rhinoviruses. The in vitro testing of the representative compounds of the invention against picornaviruses showed that picornaviral replication was inhibited at minimum inhibitory concentrations (MIC) ranging from to micrograms per milliliter (μg/ml).

The MIC values were determined by an automated tissue culture infectious dose 50% (TCID-50) assay. HeLa cells in monoloyers in 96-well cluster plates were infected with a dilution of picornavirus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from picornavirus-induced CPE relative to an untreated picornavirus control.

In the above test procedures, representative compounds of formula I were tested against some the serotypes from either a panel of fifteen human rhinopicornavirus (HRV) serotypes, (noted in the table as panel T) namely, HRV-2, -14, -1A, -1B, -6, -21, -22, -15, -25, -30, -50, -67, -89, -86 and -41 or against some of the serotypes from a panel of 10 human rhinopicornavirus serotypes namely HRV-3, -4, -5, -9, -16, -18, -38, -66, -75 and -67, (noted in the table as panel B) and the MIC value, expressed in micrograms per milliliter (mg/ml), for each rhinopicornavirus serotype was determined for each picornavirus, example le is given as an example of the data. Then $MIC_{50}$ values, which are the minimum concentrations of the compound required to inhibit 50% of the tested serotypes were determined. The compounds tested were found to exhibit antipicornaviral activity against one or more of these serotypes.

The following Table gives the test results for representative compounds of the invention. The panel of picornaviruses used in the test appears before the the $MIC_{80}$ and $MIC_{50}$ figure and the number of serotypes which the compound is tested against (N) is indicated after the $MIC_{80}$ and $MIC_{50}$ figure.

TABLE

| Ex No. | Panel | Mic₅₀ | N |
|---|---|---|---|
| 1a | B | 3.47 | 2 |
| 1c₁ | B | 1.27 | 3 |
| 1c₂ | T | 0.23 | 9 |
| 2c | B | 0.45 | 3 |
| 3 | B | 0.033 | 10 |
| 4 | B | — | 10 |
| 5c | T | 3.143 | 3 |
| 5d | T | 5.952 | 15 |
| 6c | T | 0.153 | 15 |
| 7d | T | 0.25 | 14 |
| 8b | B | 0.37 | 3 |
| 8c | B | 1.1 | 3 |
| 8d | B | 0.12 | 7 |
| 9c | T | — | 13 |
| 10e | T | 0.682 | 13 |
| 10g | T | | |
| 11 | B | 0.148 | 10 |
| 11g | | | |
| 12d | B | — | 5 |
| 12f | B | 0.045 | 9 |
| 12g | B | 0.125 | 9 |
| 12h | B | 0.046 | 8 |
| 12e | B | 0.0945 | 8 |
| 13d | B | 0.172 | 9 |
| 14d | B | 0.51 | 9 |
| 15c | B | 0.71 | 7 |
| 15e | B | 0.23 | 9 |
| 15f | B | 0.2 | 8 |
| 15g | B | 0.47 | 8 |
| 18a | T | 0.172 | 13 |
| 18b | T | 0.1225 | 12 |
| 18c | T | 0.27 | 15 |
| 18e | T | 2.697 | 11 |
| 19 | B | 0.62 | 10 |

Many of the example compounds are quite active. against one or more of the serotypes tested, thus the $MIC_{50}$ is inadequate to describing their utility. Examples of the biological data follow, $MIC_{50}$ is listed after each serotype.

| Ex. | Serotype ($MIC_{50}$) |
|---|---|
| 10 F | R6-(0.502) |
| 10 G1 | R86-(5.316), R41-(2.186) |
| 10 G2 | IA |
| 10 G3 | IA |
| 10 G4 | R15-(2.4734), R30-(0.457) |
| 10 G5 | IA |
| 16 | R1B-(0.186); R21-(0.033); R89-(0.043) |
| 17 E | R38-(0.341) |
| 17 F | R38-(0.415); R16-(0.714) |
| 17 H | R38-(0.449) |
| 18 F | R1B-(0.268); R22-(0.09); R30-(0.071); R50-(0.192); R4-(0.663) |
| 19 B | R1B-(0.268); R22-(0.09); R30-(0.071), R50-(0.192); R41-(0.663) |

Formulations of the Invention

The compounds of formula I can be formulated into compositions, including sustained release compositions together with one or more non-toxic physiologically acceptable carriers, adjuvants or vehicles which are collectively referred to herein as carriers, in any conventional form, using conventional formulation techniques for preparing compositions for treatment of infection or for propylactic use, using formulations well known to the skilled pharmaceutical chemist, for parenteral injection or oral or nasal administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as an aerosal, for example as a nasal or a buccal spray.

Compositions suitable for parenteral injection can comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, polyalkylene glycols and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders, lozenges and granules which may be dissolved slowly in the mouth, in order to bathe the mouth and associated passages with a solution of the active ingredient. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms can also comprise buffering agents.

Certain solid dosage forms can be delivered through the inhaling of a powder manually or through a device such as a SPIN-HALER used to deliver disodium cromoglycate (INTAL). When using the latter device, the powder can be encapsulated. When employing a liquid composition, the drug can be delivered through a nebulizer, an aerosol vehicle, or through any device which can divide the composition into discrete portions, for example, a medicine dropper or an atomizer.

Solid compositions of a similar type may also be formulated for use in soft and hard gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They can contain opacifying agents, and can also be of such composition that they release the active compound or compounds in a certain part of the intestinal tract in a delayed manner.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. Also solid formulations can be prepared as a base for liquid formulations. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, can contain suspending agents, as for example, ethoxylated isostearyl alcohols, polyoxyethylene sorbitol, polyethyleneglycols of varying molecular weights and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Compositions for administration as aerosols are prepared by dissolving a compound of Formula I in water or a suitable solvent, for example an alcohol ether, or other inert solvent, and mixing with a volatile propellant and placing in a pressurized container having a metering valve to release the material in usefule droplet size.

The liquefied propellant employed typically one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or a alkyl chloride, such as methyl, ethyl, or propyl chlorides. Further suitable liquefied propellants are the fluorinated and fluorochlorinated alkanes such as are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. Typically, one uses a cosolvent, such as an ether, alcohol or glycol in such aerosol formulations.

The specifications for unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for ingestion or, aerosols with metered discharges, segregated multiples of any of the foregoing, and other forms as herein described.

Compounds of the invention are useful for the prophylaxis and treatment of infections of suspected picornaviral etiologies such as aseptic meningitis, upper respiratory tract infection, enterovirus infections, coxsackievirus, enteroviruses and the like. An effective but non-toxic quantity of the compound is employed in treatment. The dosage of the compound used in treatment depends on the route of administration, e.g., intra nasal, intra bronchial, and the potency of the particular compound.

Dosage forms for topical administration include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated.

It will be appreciated that the starting point for dosage determination, both for prophylaxis and treatment of picornaviral infection, is based on a plasma level of the compound at roughly the minimum inhibitory concentration levels determined for a compound in the laboratory. For example a MIC of 1 $\mu$g/mL would give a desired starting plasma level of 0.1 mg/dl and a dose for the average 70 Kg mammal of roughly 5 mg. It is specifically contemplated that dosage range may be from 0.01–1000 mg.

Actual dosage levels of the active ingredient in the compositions can be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors and is readily determined by those skilled in the art.

The formulation of a pharmaceutical dosage form, including determination of the appropriate ingredients to employ in formulation and determination of appropriate levels of active ingredient to use, so as to achieve the optimum bioavailability and longest blood plasma halflife and the like, is well within the purview of the skilled artisan, who normally considers in vivo dose-response relationships when developing a pharmaceutical composition for therapeutic use.

Moreover, it will be appreciated that the appropriate dosage to achieve optimum results of therapy is a matter well within the purview of the skilled artisan who normally considers the dose-response relationship when developing a regimen for therapeutic use. For example the skilled artisan may consider in vitro minimum inhibitory concentrations as a guide to effective plasma levels of the drug. However, this and other methods are all well within the scope of practice of the skilled artisan when developing a pharmaceutical.

It will be understood that the specific dose level for any particular patient will depend upon a variety of factors including the body weight, general health, sex, diet, time and route of administration, rates of absorption and excretion, combination with other drugs and the severity of the disease being treated and is readily determined by the skilled clinician.

When administered prior to infection, that is, prophylactically, it is preferred that the administration be within about 0 to 48 hours prior to infection of the host animal with the pathogenic picornavirus. When administered therapeutically to inhibit an infection it is preferred that the administration be within about a day or two after infection with the pathogenic virus.

The dosage unit administered will be dependent upon the picornavirus for which treatment or prophylaxis is desired, the type of animal involved, its age, health, weight, extent of infection, kind of concurrent treatment, if any, frequency of treatment and the nature of the effect desired.

The compound of the invention also finds utility in preventing the spread of picornaviral infection. the compounds can be used in aerosol sprays applied to contaminated surfaces, to disposable products, such as tissues and the like used by an infected person. In addition the compounds can be used to impregnate household products such as tissues, other paper products, disposable swabs, and the like to prevent the spread of infection by inactivating the picornavirus.

Because compounds of the invention are able to suppress the growth of picornaviruses when added to a medium in which the picornavirus is growing, it is specifically contemplated that compounds of the invention can be used in disinfecting solutions, for example in aqueous solution with a surfactant, to decontaminate surfaces on which polio, Coxsackie, rhinovirus and/or other picornaviruses are present, such surfaces including, but not limited to, hospital glassware, hospital working surfaces, restuarant tables, food service working surfaces, bathroom sinks and anywhere else that it is expected that picornaviruses may be harbored.

Hand contact of nasal mucus may be the most important mode of rhinovirus transmission. Sterilization of the hands of people coming into contact with persons infected with rhinovirus prevents further spread of the disease. It is contemplated that a compound of the invention incorporated into a hand washing or hand care procedure or product, inhibits production of rhinovirus and decreases the likelihood of the transmission of the disease.

We claim:

1. A compound of formula:

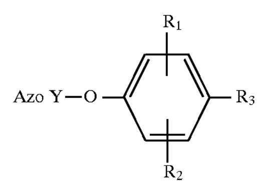

Formula I wherein

- Azo is alkyltetrazolyl or is chosen from the group consisting of imidazolyl, pyrazolyl, triazinyl, triazolyl, and oxazolyl, optionally substituted with a member of the group consisting of alkyl, alkylthio, alkoxy, hydroxy, halo, cyano, nitro, hydroxyalkyl, alkoxyalkyl, alkoxycarbonyl, alkanoyl, fluoroalkyl or the N-oxide of any of the preceding;
- Y is an alkylene bridge of 3–9 carbon atoms;
- $R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;
- $R_3$ is alkoxycarbonyl, phenyl, alkyltetrazolyl, or a heterocycle chosen from benzoxazolyl, benzathiazolyl, thiadiazolyl, imidazolyl, dihydroimidazolyl oxazolyl, thiazolyl, oxadiazolyl, pyrazolyl, isoxazolyl, isothiazolyl, furyl, triazolyl, thiophenyl, pyridyl pyrimidinyl, pyrazinyl, pyridazinyl or of substituted phenyl or substituted heterocyclyl wherein the substitution is with alkyl, alkoxyalkyl, cycloalkyl, haloalkyl, hydroxyalkyl, alkoxy, hydroxy, furyl, thienyl or fluoroalkyl; the N-oxide thereof; or a pharmaceutically acceptable acid addition salt thereof.

2. A compound according to claim 1 wherein Y is a linear hydrocarbon chain of 3 to about five carbons.

3. A compound according to claim 2 wherein $R_3$ is substituted oxadiazolyl or tetrazolyl.

4. A compound according to claim 3 wherein $R_3$ is chosen from the group consisting of 5-trifluoromethyl-1,2,4-oxadiazolyl, 5-fluoromethyl-1,2,4-oxadiazolyl, 5-difluoromethyl-1,2,4-oxadiazolyl and 2-methyl-5H-tetrazolyl.

5. A pharmaceutical composition containing as an active ingredient an antipicornavirally effective amount of a compound according to claim 1.

6. A pharmaceutical composition containing as an active ingredient an antipicornavirally effective amount of a compound according to claim 3.

7. A pharmaceutical composition containing as an active ingredient an antipicornavirally effective amount of a compound according to claim 4.

8. A method of preventing or treating picornaviral infection in a mammalian host comprising administering an antipicornavirally effective amount of a compound according to claim 1.

9. A method of preventing or treating picornaviral infection in a mammalian host comprising administering an antipicornavirally effective amount of a compound according to claim 3.

10. A method of preventing or treating picornaviral infection in a mammalian host comprising administering an antipicornavirally effective amount of a compound according to claim 4.

11. A method of combating picornaviruses comprising contacting the locus of said viruses with a compound of claim 1.

12. A method of combating picornaviruses comprising contacting the locus of said viruses with a compound of claim 3.

13. A method of combating picornaviruses comprising contacting the locus of said viruses with a compound of claim 5.

* * * * *

UNITED STATES PATENT AND TRADEMARK OFFICE
CERTIFICATE OF CORRECTION

PATENT NO. : 5,846,986
DATED : December 8, 1998
INVENTOR(S) : David J. Aldous et al.

It is certified that error appears in the above-identified patent and that said Letters Patent is hereby corrected as shown below:

Column 38, line 22:   In Claim 13, "claim 5" should read as -- claim 4 --.

Signed and Sealed this

Twenty-first Day of November, 2000

Attest:

Q. TODD DICKINSON

*Attesting Officer*   *Director of Patents and Trademarks*